United States Patent
Wehner et al.

(12) 
(10) Patent No.: US 6,218,387 B1
(45) Date of Patent: Apr. 17, 2001

(54) VITRONECTIN RECEPTOR ANATAGONISTS, THEIR PREPARATION AND THEIR USE

(75) Inventors: Volkmar Wehner, Sandberg; Hans Ulrich Stilz, Frankfurt; Anuschirwan Peyman, Kelkheim; Karlheinz Scheunemann, Liederbach, all of (DE); Jean-Marie Ruxer, Issy les Moulineaux (FR); Denis Carniato, Marcoussis (FR); Jean-Michel Lefrancois, Livry Gargan (FR); Thomas Richard Gadek, Oakland; Robert McDowell, San Francisco, both of CA (US)

(73) Assignees: Hoechst Aktiengesellschaft, Frankfurt am Main (DE); Genetech, Inc., South San Francisco, CA (US)

( * ) Notice: Subject to any disclaimer, the term of this patent is extended or adjusted under 35 U.S.C. 154(b) by 0 days.

(21) Appl. No.: 09/412,314

(22) Filed: Oct. 5, 1999

Related U.S. Application Data

(62) Division of application No. 08/995,522, filed on Dec. 22, 1997, now Pat. No. 5,990,145.

(30) Foreign Application Priority Data

Dec. 20, 1996 (DE) ............................................. 196 53 646

(51) Int. Cl.[7] ...................... C07D 243/20; A61K 31/551; A61P 19/10
(52) U.S. Cl. .......................... 514/220; 514/221; 540/506; 540/495
(58) Field of Search .................................. 540/506, 495; 514/221, 220

(56) References Cited

FOREIGN PATENT DOCUMENTS

| | | |
|---|---|---|
| 196 28 817 | 1/1998 | (DE) . |
| 196 29 816 | 1/1998 | (DE) . |
| 0 528 586 | 2/1993 | (EP) . |
| 0 528 587 | 2/1993 | (EP) . |
| 531 883 | 3/1993 | (EP) . |
| 741 133 | 11/1996 | (EP) . |
| 0 796 855 | 9/1997 | (EP) . |
| 93/00095 | 1/1993 | (WO) . |
| 94/08577 | 4/1994 | (WO) . |
| 94/12181 | 6/1994 | (WO) . |
| 94/14776 | 7/1994 | (WO) . |
| 95/18111 | 7/1995 | (WO) . |
| 95/32710 | 12/1995 | (WO) . |
| 96/00574 | 1/1996 | (WO) . |
| 96/00730 | 1/1996 | (WO) . |
| 96/26190 | 8/1996 | (WO) . |
| 97/01540 | 1/1997 | (WO) . |
| 97/24122 | 7/1997 | (WO) . |
| 97/24124 | 7/1997 | (WO) . |
| 97/24119 | * 7/1997 | (WO) . |

OTHER PUBLICATIONS

Horton et al., "Arg–Gly–Asp (RGD) Peptides and the Anti–Vitronectin Receptor Antibody 23C6 Inhibit Dentine Resorption and Cell Spreading by Osteoclasts[1]" *Experimental Cell Research 195*, pp. 368–375 (1991).

Sato et al, "Echistatin Is a Potent Inhibitor of Bone Resorption in Culture" *The Journal of Cell Biology* 111:1713–1723 (1990).

Fisher et al., "Inhibition of Osteoclastic Bone Resorption in Vivo by Echistatin, An "Arginyl–glycyl–Aspartyl" (RGD)–Containing protein" *Endocrinology* 132:1411–1413 (1993).

Brown et al., "Stimulation of migration of human aortic smooth muscle, cell by vitronection: implications for atherosclerosis" *Cardiovascular Research* 28:1815–1820 (1994).

Brooks et al., "Integrin $A_v$ $B_v$ Antagonists Promote Tumor Regression by Inducing Apoptosis of Angiogenic Blood Vessels" *Cell* 79:1157–1164 (1994).

Friedlander et al., "Definition of Two Angiogenic Pathways by Distinct $a_v$ integrins" *Science* 270:1500–1502 1995.

Engleman et al., A Peptidomimetic Antagonist of the $a_vB_3$ Integrin Inhibits Bone Resorption in Vitro and Prevents Osteoporosis in Vivo *J. Clin. Invest.* 99:2284–2292 (1997).

* cited by examiner

*Primary Examiner*—Richard L. Raymond
*Assistant Examiner*—Hoang Liu
(74) *Attorney, Agent, or Firm*—Foley & Lardner

(57) ABSTRACT

The present invention relates to compounds of the formula I, $$A-B-D-E-F-G \qquad (I)$$

in which A, B, D, E, F and G have the meanings given in the patent claims, to their preparation and to their use as medicaments. The compounds of the invention are used as vitronectin receptor antagonists and as inhibitors of bone resorption.

12 Claims, No Drawings

VITRONECTIN RECEPTOR ANATAGONISTS, THEIR PREPARATION AND THEIR USE

This is a divisional application of Ser. No. 08/995,522, filed Dec. 22, 1997, now U.S. Pat. No. 5,990,145.

The present invention relates to compounds of the formula I $$A—B—D—E—F—G \qquad (I)$$

in which A, B, D, E, F and G have the meanings given below, their physiologically tolerated salts and pharmaceutical preparations comprising these compounds, and to their preparation and use as vitronectin receptor antagonists for the treatment and prophylaxis of diseases which are based on the interaction between vitronectin receptors and their ligands in cell-cell or cell-matrix interaction processes, for example inflammations, cancer, tumor metastasis, cardiovascular disorders such as arteriosclerosis or restenosis, retinopathies and nephropathies, and diseases which are based on an undesirable degree of bone resorption, for example osteoporosis.

Human bones are subject to a continuous, dynamic process of reconstruction involving bone resorption and bone synthesis. These processes are regulated by cell types which are specialized for these purposes. While bone synthesis is based on the deposition of bone matrix by osteoblasts, bone resorption is based on the degradation of bone matrix by osteoclasts. Most bone disorders are based on an imbalance in the equilibrium between bone formation and bone resorption. Osteoporosis is characterized by a loss of bone matrix. Activated osteoclasts are multinuclear cells which have a diameter of up to 400 μm and which demolish bone matrix. Activated osteoclasts become attached to the surface of the bone matrix and secrete proteolytic enzymes and acids into the so-called sealing zone, i.e. the region between their cell membrane and the bone matrix. The acid environment and the proteases degrade the bone.

Studies have shown that the attachment of osteoclasts to bone is regulated by integrin receptors on the surface of the osteoclast cells.

Integrins are a superfamily of receptors which includes, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the surface of a number of cells such as endothelial cells, cells of the smooth musculature of the blood vessels, osteoclasts and tumor cells. The vitronectin receptor $\alpha_v\beta_3$ which is expressed on the osteoclast membrane regulates the process of attachment to bone and bone resorption and consequently contributes to osteoporosis. In this connection, $\alpha_v\beta_3$ binds to bone matrix proteins, such as osteopontin, bone sialoprotein and thrombospontin, which contain the tripeptide motif Arg-Gly-Asp (or RGD).

As vitronectin receptor antagonists, the novel compounds of the formula I inhibit bone resorption by osteoclasts. Bone disorders for which the novel compounds can be employed are, in particular, osteoporosis, hypercalcaemia, osteopenia, e.g. caused by metastases, dental disorders, hyperparathyroidism, periarticular erosions in rheumatoid arthritis, and Paget's disease. In addition, the compounds of the formula I may be employed for the alleviation, avoidance or therapy of bone disorders which are caused by glucocorticoid, steroid or corticosteroid therapy or by a lack of sex hormone(s). All these disorders are characterized by a loss of bone, due to an imbalance between bone synthesis and bone degradation.

Horton and coworkers describe RGD peptides and an anti-vitronectin receptor antibody (23C6) which inhibit tooth breakdown by osteoclasts and the migration of osteoclasts (Horton et al.; Exp. Cell. Res. 1991, 195, 368). In J. Cell Biol. 1990, 111, 1713, Sato et al. report that echistatin, an RGD peptide from snake venom, is a potent inhibitor of bone resorption in a tissue culture and an inhibitor of the attachment of osteoclasts to the bone. Fischer et al. (Endocrinology, 1993, 132, 1411) showed that echistatin also inhibits bone resorption in vivo in the rat.

The vitronectin receptor $\alpha_v\beta_3$ on human cells of the smooth blood vessel musculature of the aorta stimulates the migration of these cells into the neointima, thereby leading finally to arteriosclerosis and restenosis following angioplasty (Brown et al., Cardiovascular Res. 1994, 28, 1815).

Brooks et al. (Cell 1994, 79,1157) show that antibodies against $\alpha_v\beta_3$ or $\alpha_v\beta_3$ antagonists are able to shrink tumors by inducing the apoptosis of blood vessel cells during angiogenesis. Cheresh et al. (Science 1995, 270, 1500) describe anti$\alpha_v\beta_3$ antibodies or $\alpha_v\beta_3$ antagonists which inhibit bFGF-induced angiogenesis processes in the rat eye, a property which could be therapeutically useful in the treatment of retinopathies.

Patent application WO 94/12181 describes substituted aromatic or nonaromatic ring systems, and WO 94/08577 describes substituted heterocycles, which are fibrinogen receptor antagonists and inhibitors of platelet aggregation. EP-A0 528 586 and EP-A0 528 587 disdose aminoalkyl-substituted or heterocyclyl-substituted phenylalanine derivatives, and WO 95/32710 discloses aryl derivatives, which are inhibitors of bone resorption due to osteoclasts. WO 96/00574 and WO 96126190 describe benzodiazepines which are vitronectin receptor antagonists and integrin receptor antagonists, respectively. WO 96/00730 describes fibrinogen receptor antagonist templates, in particular benzodiazepines which are linked to a nitrogen-arrying 5-membered ring, which are vitronectin receptor antagonists. German patent applications P 19629816.4, P 19629817.2 and P 19610919.1 and also EP-A-0 796 855 describe substituted aromatic ring systems or 5-membered ring heterocycles which are vitronectin receptor antagonists.

The present invention relates to compounds of the formula I, $$A—B—D—E—F—G \qquad (I)$$

in which:

A is

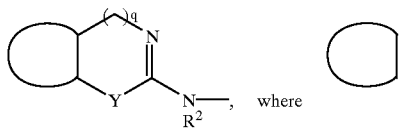

is a 5-membered to 10-membered monocyclic or polycyclic, aromatic or nonaromatic ring system which can contain from 1 to 4 heteroatoms from the group N, O and S and can optionally be substituted, once or more than once, by $R^{12}$, $R^{13}$, $R^{14}$ and $R^{15}$;

B is a direct linkage, $(C_1-C_8)$-alkanediyl, $(C_5-C_{10})$-arylene, $(C_3-C_8)$-cycloalkylene, —C≡C—, —NR²—, —NR²—C(O)—, —NR²—C(O)—NR²—, —NR²—C(S)—NR²—, —O—C(O)—, —NR²—S(O)—, —NR²—S(O)₂—, —O—, —S— or —CR²=CR³—, which can in each case be substituted, once or twice, by $(C_1-C_8)$-alkyl, for example -methyl-phenyl-methyl-, -ethyl-NR²—C(O)— etc.;

D is a direct linkage, $(C_1-C_8)$-alkanediyl, $(C_5-C_{10})$-arylene, —O—, —NR$^2$—, —CO—NR$^2$—, —NR$^2$—CO—, —NR$^2$—C(O)—NR$^2$—, —NR$^2$—C(S)—NR$^2$—, —OC(Q)—, —C(O)O—, —S(O)—, —S(O)$_2$—, —S(O)$_2$—NR$^2$—, —S(O)—NR$^2$—, —NR$^2$—S(O)—, —NR$^2$—S(O)$_2$—, —S—, —CR$^2$=CR$^3$— or —C≡C— which can in each case be substituted, once or twice, by $(C_1-C_8)$-alkyl, —CR$^2$=CR$^3$— or $(C_5-C_6)$-aryl, for example methyl-phenyl-CH=CH—, ethyl-O— etc., with it not being possible for D to be —CO—NR$^2$—, —C(O)O—, —S(O)—, —S(O)$_2$—, —S(O)—NR$^2$— or —S(O)$_2$—NR$^2$— when B is a direct linkage;

E a) is a template which is selected from the series of fibrinogen receptor antagonists and which is taken from the following patent applications, patent documents or literature references:

Adir et Compagnie
FR 928004, Jun. 30, 1992, Fauchere, J. L., et al.
EP 0578535, Jun. 29, 1993, Fauchere, J. L., et al.
CA 2128560, Jan. 24, 1995, Godfroid, J. J., et al.
Asahi Breweries, Ltd.
JP 05239030, Sep. 17, 1993.
Asahi Glass
WO 90/02751, Ohba, M. et al., Sep. 8, 1989.
WO 90/115950, Mar. 22, 1990, Ohba, M., et al.
EP 0406428, Jan. 9, 1991.
WO 92/09627, Isoai, A. et al., Nov. 29, 1991.
Chiron
WO 93/07169, (Der 93-134382/16), Mar. 15, 1993, Devlin, J. J., et al.
Ciba Geigy
EP 0452210, (Der 91-305246/42) Apr. 5, 1990.
EP 0452257, Mar. 26, 1991, Allen, M. C., et al.
COR Therapeutics
WO 90/15620, Jun. 15, 1990.
EP 0477295, Apr. 1, 1992: Scarborough, R. M., et al.
WO 92/08472, May 29, 1992, Scarborough, R. M., et al.
WO 93/223356, Apr. 27, 1993, Swift, R. L., et al.
EP 0557442, Sep. 1, 1993, Scarborough, R. M., et al.
Scarborough, R. M.; Rose, J. W.; Hsu, M. A.; Phillips, D. R.; Fried, V. A.; Campbell, A. M.; Nunnizzi, L.; Charo, I. F., Barbourin, A. GPIIb-IIIa-Specific Integrin Antagonist from the Venom of Sistrurus M. Barbouri, J. Biol. Chem, 266,9359,1991.
Daiichi Pharm Co Ltd.
JP 05078344-A, (Der 93-140339/17), Mar. 30, 1993.
DuPont Merck
WO 93/07170, Apr. 15, 1993.
WO 94/11398, May 26, 1994, Wells, G. J., et al.
IL 109237, Jul. 31, 1994.
WO 94/22909, (Der 94-333113141) Oct. 13, 1994: DeGrado W. F., et al.
WO 94/22910, (Der 94-333114/41) Oct. 13, 1994: DeGrado W. F., et al.
WO 94/22494, (Der 94-332838/41) Oct. 13, 1994: DeGrado W. F., et al.
EP 625164, Nov. 23, 1994: Degrado, W. F., et al.
WO 95/14682, Jun. 1, 1995, Wityak, J., et al.
WO 95/14683, Jun. 1, 1995, Wityak, J., et al.
WO 95/18111, Jul. 6, 1995, DeGrado, W. F., et al.
WO 95/23811, Sep. 8, 1995, DeGrado, W. F., et al.
Mousa, S. A.; Bozarth, J. M.; Forsythe, M. S.; Jackson, S. M., Leamy, A.;
Diemer, M. M.; Kapil, R. P.; Knabb, R. M.; Mayo, M. C.; Pierce, S. K.; al., e., Antiplatelet and Antithrombotic Efficacy of DMP 728, a Novel Platelet GPIIb/IIIa Receptor Antagonist, Circulation, 89, 3, 1994.
Jackson, S.; DeGrado, W.; Dwivedi, A.; Parthasarathy, A.; Higley, A.; Krywko, J.; Rockwell, A.; Markwalder, J.; Wells, G.; Wexler, R.; Mousa, S.; Harlow, R., Template-Constrained Cyclic Peptides: Design of High-Affinity Ligands for GPIIb/IIIa, J. Amer. Chem. Soc., 116,3220, 1994.
E. Merck
EP 0608759, Jan. 19, 1994, Gante, J., et al.
EP 0623615, Apr. 19, 1994, Raddatz, P., et al.
EP 0645376, Sep. 15, 1994, Gante, J., et al.
EP 0668278, Feb. 14, 1995, Juraszyk, H., et al.
EP 0697408, Aug. 10, 1995, Juraszyk, H., et al.
DE 4310643, (Der 94-311172/39), Oct. 6, 1994, Jonczyk, A., et al.
WO 9404093, Oct. 27, 1994, Jonczyk, A., et al.
EP 0632053, Jan. 4, 1995, Jonczyk, A., et al.
EP 576898, Jan. 5, 1994, Jonczyk, A., et al.
EP 0608759 A, Aug. 3, 1994, Gaute, J. P., et al.
HU 9400249, May 30, 1994, Gante, J., et al.
Ellem Ind Farma Spa
GB 2207922, Aug. 3, 1988.
Farmitalia Carlo Erba SRL
EP 611765 (Der 94-265375133), Aug. 24, 1994, Cozzi, P., et al.
Fuji Photo Film
JP 04208296-A (Der. 92-303598/38), Nov. 30, 1990.
JP 04213311-A (Der. 92-305482138), Nov. 27, 1990.
JP 04217693-A (Der. 92-312284/38), Oct. 23, 1990.
JP 04221394-A (Der. 92-313678/38), Oct. 26, 1990.
JP 04221395-A (Der. 92-313679,38), Oct. 26, 1990.
JP 04221396-A (Der. 92-313680/38), Oct. 26, 1990.
JP 04221397-A (Der. 92-313681/38), Dec. 20, 1990.
EP 0482649 A2, Apr. 29, 1992, Kojima, M., et al.
EP 0488258A2, Jun. 3, 1992, Komazawa, H., et al.
EP 0503301-A2, Feb. 14, 1991, Kitaguchi, H., et al.
JP 05222092, May 21, 1993, Nishikawa, N., et al.
JP 06239885, (Der 94-313705139), Aug. 30, 1993, Nishikawa, N., et al.
WO 9324448, (Der 93-405663/50), Dec. 9, 1993, Nishikawa, N., et al.
JP 06228189, (Der 94-299801/37), Aug. 16, 1994.
EP 0619118, (Der 94-311647/39), Oct. 12, 1994, Nishikawa, N., et al.
Fujisawa
EP 0513675, May 8, 1992, N. Umekita, et al.
WO 9409030-A1, Apr. 28, 1994, Takasugi, H., et al.
EP 0513675, (Der 92-383589/47).
WO 9500502, Jan. 5, 1995, Oku, T., et al.
WO 95/08536, Mar. 30, 1995, Ohkubo, M., et al.
FR 144633: Thromb Haem. 69, 706, 1993.
Cox, D.; Aoki, T.; Seki, J.; Motoyama, Y.; Yoshida, K, Pentamidine: A Specific Nonpeptide GPIIb/IIIa Antagonist, Thromb. Haem., 69, 707, 1993.

Genentech
WO 90/15072 (Der 91007159).
WO 91/01331 (Der 91058116), Jul. 5, 1990, P. L. Barker, et al.
WO 91/04247, Sep. 24, 1990, T. R. Webb.
WO 91111458 (Der 91252610), Jan. 28, 1991, P. L. Barker, et al.
WO 92/07870, Oct. 24, 1991 J. P. Burnier, et al.
WO 92/17492, Oct. 15, 1992, Burnier, J. P., et al.
U.S. Pat. No. 5,250,679, Oct. 5, 1993, Blackburn, B. K, et al.
U.S. Pat. No. 5,403,836, Apr. 4, 1995, Blackburn, B. K, et al.
U.S. Pat. No. 5,565,449 Oct. 15, 1996, Blackburn, B. K, et al.
CA 2106314, Oct. 6, 1992, Burnier, J. P., et al.
WO 93108174, Oct. 15, 1991, B. K. Blackburn, et al.
CA 2106314, Oct. 6, 1992, Burnier, J. P., et al.
EP 0555328, Aug. 18, 1993, J. P. Burnier, et al.
WO 95104057, Feb. 9, 1995, Blackburn, B. K., et al.
Scarborough, R. M., Naughton, M. A., Teng, W., Rose, J. W., Phillips, D. R., Nannizzi, L., Arfsten, A., Campbell, A. M., and Charo, I. F., J. Biol. Chem. 268, 1066,1993.
Dennis, M. S.; Henzel, W. J.; Pitti, R. M.; T., L. M.; Napier, M. A.; Deisher, T. A.; Bunting, S.; Lazarus, R., Platelet Glycoprotein IIb-IIIa Protein Antagonists from Snake Venoms: Evidence for a Family of Platelet-Aggregation Inhibitors, Proc. Natl. Acad. Sci. USA, 87, 2471, 1989.
Barker, P. L.; Bullens, S.; Bunting, S., Burdick, D. J.; Chan, K. S.; Deisher, T.; Eigenbrot, C.; Gadek, T. R.; Gantzos, R.; Lipari, M. T.; Muir, C. D.; Napier, M. A.; Pitti, R. M.; Padua, A.; Quan, C.; Stanley, M.; Struble, M.; Tom, J. Y. K.; Bunier, J., P., Cyclic RGD Peptide Analogues as Antiplatelet Antithrombotics, J. Med. Chem., 35, 2040,1992.
McDowell,. R. S.; Gadek, T. R., Structural Studies of Potent Constrained RGD Peptides, J. Amer. Chem Soc., 114, 9245,1992.
Glaxo
EP 0537980, Oct. 13, 1992, B. Porter, et al.
EP 0542363, Nov. 10, 1992, Porter, B., et al.
WO 93110091, May 27, 1993, Porter, B., et al.
WO 93114077, Jul. 22, 1993, Porter, B., et al.
WO 93/22303, Jan. 11, 1993, Middlemiss, D., et al.
WO 93114077, Jan. 15, 1993, B. Porter, et al.
EP 0609282 A1, Aug. 10, 1994, Porter, B., et al.
EP 0612313, Aug. 31, 1994, Porter, B., et al.
EP 903911769, Apr. 20, 1994, Middlemiss, D., et al.
EP 0637304 A1, Feb. 8, 1995, Middlemiss, D., et al.
Hann, M. M.; Carter, B.; Kitchin, J.; Ward, P.; Pipe, A.; Broomhead, J.; Horuby, E.; Forster, M.; Perry, C., An Investigation of the Bioactive Conformation of ARG-GLY-ASP Containing Cyclic Peptides and Snake Venom Peptides which Inhibit Human Platelet Aggregation, In Molecular Recognition: Chemical and Biochemical Problems II, S. M. Roberts, Ed., The Royal Society of Chemistry, Cambridge, 1992.
Ross, B. C. Nonpeptide Fibrinogen Receptor Antagonists, (SAR leading to the discovery of GR 144053), In Seventh RSC-SCI Medicinal Chemistry Symposium, The Royal Society of Chemistry Fine Chemicals and Medicinals Group and SCI Fine Chemicals Group, Churchill College, Cambridge, 1993, L20.
Pike, N. B.; Foster, M. R.; Homby, E. J.; Lumley, P., Effect of the Fibrinogen Receptor Antagonist GR144053 Upon Platelet Aggregation Ex Vivo Following Intravenous and Oral Administration to the Marmoset and Cynomologous Monkey, Thromb. Haem., 69, 1071, 1993.
Hoffmann-La Roche
AU 9344935, (Der 94-118783/15), Mar. 10, 1994.
EP 0592791, Apr. 20, 1994, Bannwarth. W., et al.
Kogyo Gijutsuin
JP 06179696, Jun. 28, 1994, Maruyama, S., et al.
Kyowa Hakko Kogyo KK
JP 05078244-A, Mar. 30, 1993.
Laboratoire Chauvin
WO 9401456, Jan. 20, 1994, Regnouf, D. V. J., et al.
La Jolla Cancer Res. Fndn
WO 9500544, Jan. 5, 1994, Pierschbacher, M. D., et al.
U.S. Pat. No. 0,794,41, Jan. 5, 1994, Pierschbacher, M. D., et al.
Lilly/COR
EP 0635492, Jan. 25, 1995, Fisher, M. J., Happ, A. M., Jakubowski, J. A. Kinnick,
M. D., Kline, A. D., Morin, Jr., J. M., Sall, M. A, Vasileff, R. T.
EP 0655439, Nov. 9, 1994, Denney, M. L., et al.
Medical University of South Carolina
EP 587770, Mar. 23, 1994, Halushka, P. V., Spicer, K. M.
Merck
EP 0368486 (Der 90-149427/20), Nov. 10, 1988.
EP 0382451 (Der 90248531).
EP 0382538 (Der 90248420).
EP 0410537, Jul. 23, 1990, R. F. Nutt, et al.
EP 0410539, Jul. 25, 1990, R. F. Nutt, et al.
EP 0410540, Jul. 25, 1990, R. F. Nutt, et al.
EP 0410541, Jul. 25, 1990, R. F. Nutt, et al.
EP 0410767, Jul. 26, 1990, R. F. Nutt, et al.
EP 0411833, Jul. 26, 1990, R. F. Nutt, et al.
EP 0422937, Oct. 11, 1990, R. F. Nutt, et al.
EP 0422938, Oct. 11, 1990, R. F. Nutt, et al.
EP 0487238, Oct. 13. 1991, T. M. Connolly, et al.
EP 0437367 (Der 91209968), M. Sato, et al.
WO 9409029, Apr. 28, 1994, Nutt, R. F. and Veber, D. F.
EP 618225, (Der 94-304404/38) Oct. 5, 1994.
EP 0479481, Sep. 25, 1991, M. E. Duggan, et al.
EP 0478362, Sep. 27, 1991 M. E. Duggan, et al.
EP 0512831, May 7, 1992, Duggan, M. E., et al.
EP 0540334, Oct. 29, 1992, G. D. Hartman, et al.
U.S. Pat. No. 5,264,420-A, Nov. 23, 1993.
U.S. Pat. No. 5,272,158, Dec. 21, 1993, Hartmann G. D., et al.
U.S. Pat. No. 5,281,585, Jan. 25, 1994, Ihle, N., et al.
GB 945317 A, Mar. 17, 1994 (Priority U.S. Pat. No. 34,042A, Mar. 22, 1993).
GB 2271567 A, Apr. 20, 1994, Hartman, G. D., et al.
WO 9408962, Apr. 28, 1994, Hartmann, G. D., et al.
WO 9409029, (Der 94-151241/18) Apr. 28, 1994, Hartman, G. D., et al.

U.S. Pat. No. 5,321,034, Jun. 14, 1994, Duggan, M. E., et al.
U.S. Pat. No. 5,334,596, Aug. 2, 1994, Hartman, G. D., et al.
U.S. Pat. No. 5,328,900, Jul. 12, 1994, Klein, S. I., et al.
U.S. Pat. No. 5,332,726, Jul. 26, 1994, Klein, S. I., et al.
U.S. Pat. No. 5,451,578, Sep. 19, 1995, Claremon, D. A., et al.
U.S. Pat. No. 5,455,243, Oct. 3, 1995, Duggan, M. E., et al.
WO 9418981, (Der 94-293975/36) Sep. 1, 1994, Claremon, D. A., et al.
GB 2276384, (Der 94-287743/36) Sep. 28, 1994, Claremon, D. A, Liverton, N.
WO 9422825, Oct. 13, 1994, Claremon, D. A, Liverton, N. J.
WO 9504531, Feb. 16, 1995, Hartman, G. D., et al.
WO 95/17397, Jun. 29, 1995, Hartmann, G. D., et al.
Nutt, R. F.; Brady, S. F.; Colton, C. D.; Sisko, J. T.; Ciccarone, T. M.; Levy, M. R.; Duggan, M. E.; Imagire, I. S.; Gould, R. J.; Anderson, P. S.; Veber, D. F., Development of Novel, Highly Selective Fibrinogen Receptor Antagonists as Potentially Useful Antithrombotic Agents, In Peptides, Chemistry and Biology, Proc. 12th Amer. Peptide Symp., J. A. Smith and J. E. Rivier, Ed., ESCOM, Leiden, 1992; 914.
Hartman, G. D.; Egbertson, M. S.; Halszenko, W.; Laswell, W. L.; Duggan, M. E.; Smith, R. L.; Naylor, A. M.; Manno, P. D.; Lynch, R. J.; Zhang, G.; Chang, C. T. C.; Gould, R. J., Non-peptide Fibrinogen Receptor Antagonists. 1. Discovery and Design of Exosite Inhibitors, J. Med. Chem., 35, 4640, 1992.
Gould, R. J.; Barrett, S.; Ellis, J. D.; Holahan, M. A.; Stranieri, M. T.; Theoharides, A. D.; Lynch, J. J.; Friedman, P. A.; Duggan, M. E.; Ihle, N. C.; Anderson, P. S.; Hartman, G. D., Characterization of L-703,014, A Novel Fibrinogen Receptor Antagonist, Following Oral Administration to Dogs, Thromb. Haem., 69, 539, 1993.
Merrell Dow
WO 93/24520, May 14, 1993, Harbeson, S. L., et al.
WO 9324520, Dec. 9, 1993, Harbeson, Bitonti, J., A.
WO 9429349, Dec. 22, 1994, Harbeson, Bitonti,J., A.
Nippon Steel Corp
WO 9405696, Mar. 17, 1993, Sato, Y., et al.
EP 628571, Dec. 14, 1994, Sato, Y., et al.
WO 9501371, Jan. 12, 1995, Sato, Y., et al.
ONO Pharmaceuticals
JP 05286922 (Der 93-383035/48)
Roche
EP 038,362, Feb. 19, 1990, M. Muller, et al.
EP 0372486, Jun. 13, 1990, Allig, L., et al.
EP 0381033, Jul. 8, 1990, Allig, L., et al.
EP 0384362, Aug. 29, 1990, Allig, L., et al.
EP 0445796, Sep. 11, 1991, Allig, L., et al.
EP 0505868, Sep. 30, 1992, Allig, L., et al.
U.S. Pat. No. 5,273,982-A, (Der 94-006713/01) Dec. 28, 1993.
U.S. Pat. No. 5,430,024, Jul. 4, 1995, Allig, L., et al.
EP 0468231, Jul. 2, 1991, Ackermann, J., et al.
EP 0656348, Nov. 26, 1994, Allig, L., et al.
Allig, L.; Edenhofer, A.; Hadvary, P.; Hurzeler, M.; Knopp, D.; Muller, M.; Steiner, B.; Trzeciak, A.; Weller, T., Low Molecular Weight, Non-peptide Fibrinogen Receptor Antagonists, J. Med. Chem., 35, 4393, 1992.
Rhone-Poulenc Rorer
U.S. Pat. No. 4,952,562, Sep. 29, 1989, S. I. Klein, et al.
U.S. Pat. No. 5,064,814, (Der 91-353169/48) Apr. 5, 1990.
WO 9104746, Sep. 25, 1990, S. I. Klein, et al.
WO 91/05562, Oct. 10, 1989, S. I. Klein, et al.
WO 91/07976, (Der 91-192965) Nov. 28, 1990, S. I. Klein, et al.
WO 91/04746, S. I. Klein, et al.
WO 92118117, Apr. 11, 1991, S. I. Klein, et al.
U.S. Pat. No. 5,086,069, (Der 92 064426/08) Apr. 2, 1992.
WO 92/17196, Mar. 30, 1992, S. I. Klein, et al.
U.S. Pat. No. 5,328,900, (Der 94-221950/27) Jul. 12, 1992.
U.S. Pat. No. 5,332,726, (Der 94-241043/29) Jul. 26, 1994.
WO 93/11759, Dec. 7, 1992, S. I. Klein, et al.
EP 0577775, Jan. 12, 1994, Klein, S. I., et al.
WO 95/10295, Apr. 20, 1995, Klein, S. I., et al.
CA 2107088, Sep. 29, 1992, Klein, S. I., et al.
Sandoz
EP 0560730, Mar. 8, 1993, G. Kottirisch and R. Mettemich.
G. Kottirisch, et al. Biorg. Med. Chem. Lett 3, 1675–1680, 1993.
Schering AG
EP 530937, Mar. 10, 1993, Noeski-Jungblut, C., et al.
Searle/Monsanto
EP 0319506, (Der 89-3195506) Dec. 2, 1988, S. P. Adams, et al.
EP 0462,960, Jun. 19.1991, Tjoeng, F. S., et al.
U.S. Pat. No. 4,857,508, S. P. Adams, et al.
EP 0502536, (Der 92-301855) Mar. 3, 1991, R. B. Garland, et al.
EP 0319506, Dec. 2, 1988, S. P. Adams, et al.
U.S. Pat. No. 4,992,463, Aug. 18, 1989.
U.S. Pat. No. 5,037,808, Apr. 23, 1990.
EP 0454651 A2, Oct. 30, 1991, Tjoeng, F. S., et al.
U.S. Pat. No. 4,879,313, Jul. 20, 1988.
WO 93/12074, Nov. 19, 1991, N. Abood, et al.
WO 93/12103, Dec. 11, 1991, P. R. Bovy, et al.
U.S. Pat. No. 5,091,396, Feb. 25, 1992, Tjoeng, F. S., et al.
WO 92/15607, Mar. 5, 1992, Garland, R. B., et al.
WO 93107867, Apr. 29, 1993, P. R. Bovy, et al.
U.S. Pat. No. 888,686, May 22, 1992, Bovy, P. R., et al.
CA 2099994, Sep. 7, 1992, Garland, R. B., et al.
EP 0513810, May 15, 1992, Garland, R. B., et al.
U.S. Pat. No. 5,254,573, Oct. 19, 1993, Bovy, P. R., et al.
EP 0539343, Oct. 14, 1992, P. R. Bovy, et al.
WO 93/12074, Nov. 27, 1992, N. A. Abood, et. al.
WO 93/12103, Dec. 11, 1992, P. R. Bovy, et al.
EP 0539343, Apr. 28, 1993, Bovy, P. R., et al.
EP 0542708, May 19, 1993, Bovy. P. R., et al.

WO 94/00424, Jan. 6, 1994, Abood, N. A, et al.
WO 93/16038, Aug. 16, 1993, Miyano. M., et al.
WO 93US7975, Aug. 17, 1993, Zablocki, J. A., Tjoeng, F. S.
WO 93/18058, Sep. 16, 1993, Bovy, P. R., et al.
U.S. Pat. No. 5,254,573, Oct. 19, 1993, Bovy, P. R., et al.
U.S. Pat. No. 5,272,162, Dec. 21, 1993, Tjoeng, F. S., et al.
EP 0574545, Dec. 22, 1993, Garland, R. B., et al.
WO 9401396, Jan. 20, 1994, Tjoeng, F. S., et al.
WO 9405694, (Der 94-101119/12) Mar. 17, 1994, Zablocki, et al.
U.S. Pat. No. 5,314,902, May 24, 1994, Adams, S. P., et al.
WO 9418162, Aug. 18, 1994, Adams, S. P., et al.
WO 9419341, Sep. 1, 1994, Tjoeng, F. S., et al.
U.S. Pat. No. 5,344,837, (Der 94-285503/35), Sep. 6, 1994, Zablocki, J. A., et al.
EP 614360, Sep. 14, 1994, Bovy, P. R., et al.
WO 9420457, (Der 94-302907/37), Sep. 15, 1994, Tjoeng, F. S., et al.
WO 9421602, (Der 94-316876/39), Sep. 29, 1994, Tjoeng, F. S., et al.
WO 9422820, Oct. 13, 1994, Abood, N. A., et al.
EP 630366, Dec. 28, 1994, Bovy, P. R., et al.
U.S. Pat. No. 5,378,727, Jan. 3, 1995, Bovy, P. R., et al.
WO 95106038, Mar. 2, 1995, Bovy P. R., et al.
WO 93/08164, Apr. 29, 1993, Bovy, P. R., et al.
K. F. Fok, et al., Int. J. Peptide Prot. Res., 38, 124–130, 1991, SAR of RGDY analogs.
J. A. Zablocki, et al. J. Med. Chem. 35, 4914–4917, 1992, SAR summary of guanidinoalkanoyl-Asp-Phe analogs.
Tjoeng, F. S.; Fok, K. F.; Zupec, M. E.; Garland, R. B.; Miyano, M.; Panzer-Knodle, S.; King, L. W.; Taite, B. B.; Nicholson, N. S.; Feigen, L. P.; Adams, S. P., Peptide Mimetics of the RGD Sequence, In Peptides, Chem. and Biol. Proc. 12th Amer. Peptide Symp., J. A. Smith and J. E. Rivier, Ed., ESCOM, Leiden, 1992; 752.
Nicholson, N.; Taite, B.; Panzer-Knodle, S.; Salyers, A.; Haas, N.; Szalony, J.; Zablocki, J.; Feigen, L.; Glenn, K.; Keller, B.; Broschat, K.; Herin, M.; Jacqmin, P.; lesne, M., An Orally Active Glycoprotein IIb/IIIa Antagonist-SC-54684, Thromb. Haem, 69, 975, 1993.
Smithkline Beecham Corporation
WO 91/07429, May 30, 1991, Ali, F., et al.
WO 92/07568, May 14, 1992, Callahan, J. F., et al.
WO 92113552, Aug. 20, 1992, Ali, F., et al.
WO 93/00095, Jan. 7, 1993, Bondinell, W. E., et al.
WO 93/09133, May 13, 1993, Callahan, J. F., et al.
WO 94/12478, Jun. 9, 1994, Keenan, R. M. C., et al.
WO 94/14775, Jul. 7, 1994, Bondinell, W. E., et al.
WO 94/22440, Oct. 13, 1994, Callahan, J. F., et al.
WO 94/14776, Jul. 7, 1994, Bondinell, W. E., et al.
WO 94/15913, Jul. 21, 1994, Samanen, J.
WO 94129273, Dec. 22, 1994, Samanen, J.
WO 95/18619, Jul. 13, 1995, Bondinell, W. E., et al.
WO 96106087, Feb. 29, 1996, Kwon, C., et al.
WO 96/00730, Jan. 11, 1996, Ali, F., et al.
Sumitomo Pharm. Co. Ltd
WO 9501336, Jun. 6, 1994, Ikeda, Y., et al.
Sumitomo Seiyaku KK
JP 06025290, (Der 94-077374/10), Feb. 1, 1994.
Taisho Pharm. (Teijin, Ltd)
JP 05230009, (Der 93-317431/40), Feb. 24, 1992.
JP 9235479, Feb. 24, 1992.
WO 94/17804, Aug. 18, 1994, Mizushima, Y.
EP 0634171, Jan. 18, 1995, Nizushima, M.
Takeda
EP 0529858, Apr. 3, 1993, H. Sugihara, et al.
EP 0606881, Jul. 20, 1994.
EP 0614664, Sep. 14, 1994, Miyake, A., et al.
Tanabe
WO 89/07609, T. J. Lobi, et al.
WO 92100995, Jul. 9, 1991, T. J. Lobl, et al.
WO 93/08823, Nov. 6, 1991, T. C. McKenzie.
CA 2087021, Jan. 10, 1991, Lobl, T. J., et al.
WO 92/08464, Nov. 15, 1991, T. C. McKenzie, et al.
Telios/La Jolla Cancer Research
U.S. Pat. No. 4,578,079, Nov. 22, 1983, E. Ruoslahti, and M. Pierschbacher.
U.S. Pat. No. 4,614,517, Jun. 17, 1985, E. Ruoslahti, and M. Pierschbacher.
U.S. Pat. No. 4,792,525, Jun. 17, 1985, E. Ruoslahti, and M. Pierschbacher.
U.S. Pat. No. 4,879,237, (Der 90-154405120) May 24, 1985.
WO 91/15515, (Der 91-325173/44) Apr. 6, 1990.
U.S. Pat. No. 5,041,380, 1991, E. Ruoslahti, and M. Pierschbacher.
WO 95/00544 Jan. 5, 1995, Craig, W. S., et. al.
Cheng, S.; Craig, W. S.; Mullen, D.; Tschopp, J. F.; Dixon, D.; Pierschbacher, M. F., Design and Synthesis of Novel Cyclic RGD-Containing Peptides as highly Potent and Selective Integrin $\alpha_{IIb}\beta_3$ Antagonists, J. Medicin. Chem. 37, 1, 1994.
Colhen, D.; Lu, H. R.; Stassen, J.-M.; Vreys, I.; Yasuda, T.; Bunting, S.; Gold, H. K., Antithrombotic Effects and Bleeding Time Prolongation with Synthetic Platelet GPIIb/IIIa Inhibitors in Animal Models of Platelet-Mediated Thrombosis, Thrombosis and Haemostasis, 71, 95, 1994.
Temple U.
WO 9409036, (Der 94-151248/18), Apr. 28, 1994.
Terumo KK
JP 6279389, Oct. 4, 1994, Obama, H., et al.
Karl Thomae/Boehringer Ingelheim
EP 0483667, May 6, 1992, Himmelsbach, F., et al.
EP 0496378, Jan. 22, 1992, Himmelsbach, F., et al.
EP 0503548, Sep. 16, 1992, Himmelsbach, F., et al.
AU A-86926/91, May 7, 1992, Himmelsbach, F., et al.
EP 0528369, Feb. 24, 1993, Austel, V., et al.
EP 0537696, Apr. 21, 1993, Linz, G., et al.
DE 4124942, Jan. 28, 1993, Himmelsbach, F., et al.
DE 4129603, Mar. 11, 1993, Pieper, H., et al.
EP 0547517 A1, (Der 93-198544) Jun. 23, 1993, Soyka, R., et al.
EP 0567966, Nov. 3, 1993, Himmelsbach, F., et al.
EP 0567967, Nov. 3, 1993, Weisenberger, J., et al.
EP 0567968, Nov. 3, 1993, Linz, G., et al.

EP 0574808, Jun. 11, 1993, Pieper, H., et al.
Der 93406657/51, Austel, V., et al.
EP 587134, (Der 94-085077/11) Mar. 16, 1994, Himmelsbach, F., et al.
EP 589874, Apr. 6, 1994, Grell, W., et al.
(P534005), DE 4234295, Apr. 14, 1994, Pieper, H., et al.
EP 0592949, Apr. 20, 1994, Pieper, H. D., et al.
EP 0596326, May 11, 1994, Maier, R., et al.
DE 4241632, Jun. 15, 1994, Himmelsbach, F., et al.
EP 0525629, Jul. 22, 1992, Himmelsbach, F., et al.
EP 0531883, Sep. 3, 1992, Austel, V., et al.
EP 0604800 A, Jul. 6, 1994, Himmelsbach, F., et al.
DE 4302051, (Der 94-235999/29) Jul. 28, 1994.
EP 0608858 A, Aug. 3, 1994, Linz, G. D., et al.
DE 4304650, (Der 94-256165/32), Aug. 18, 1994, Austel, V., et al.
EP 611660, Aug. 24, 1994, Austel, V., et al.
EP 0612741, Feb. 21, 1994, Himmelsbach, F., et al.
DE 4305388, (Der 94-264904/33), Aug. 25, 1994, Himmelsbach, F., et al.
EP 612741, (Der 94-265886/33), Aug. 31, 1994, Himmelsbach, F., et al.
EP 0639575 A, Feb. 22, 1995, Linz, G., et al.
DE 4324580, Jan. 26, 1995, Linz, G., et al.
EP 0638553, Feb. 15, 1995, Himmelsbach, F., et al.
WO 95/24405, Sep. 14, 1995, Himmelsbach, F., et al.
WO 96/02514, Feb. 1, 1996, Himmelsbach, F., et al.
WO 96/02504, Feb. 1, 1996, Himmelsbach F., et al.
DE 4427838, Feb. 8, 1996, Himmelsbach, F., et al.
WO 96/05194, Feb. 22, 1996, Himmelsbach, F., et al.
DE 4431868, Mar. 14, 1996, Pieper, H., et al.
DE 4429079, Feb. 22, 1996, Himmelsbach, F., et al.
F. Himmelsbach, V. Austel, G. Kruger, H. Pieper, H. Weisenberger, T. H. Muller, and W. G. Eisert, in XIIth Int. Symp. on Med. Chem. Basel, Book of Abstracts, 47, 1992.
V. Austel, W. Eisert, F. Himmelsbach, G. Kruger, G. Linz, T. Muller, H. Pieper, and J. Weisenberger, Natl. Mtg. Amer. Chem. Soc. Book of Abstracts, Denver, Div. Med. Chem., 1993.
Muller, T. H.; Schurer, H.; Waldmann, L.; Bauer, E.; Himmelsbach, F.; Binder, K, Orally Activity of BIBU 104, a Prodrug of the Non-peptide Fibrinogen Receptor Antagonist BIBU 52, in Mice and Monkeys, Thromb. Haem., 69, 975, 1993.
Univ. California
WO 94/14848, Jul. 7, 1994, Zanetti, M.
Univ. New York
WO 94/00144, Jun. 29, 1993, Ojima, I., et al.
Yeda Res. and Dev. Co.
WO 93/09795, (Der 93-182236/22), Lido, O., et al.
Zeneca
WO 9422834, Oct. 13, 1994, Wayne, M. G., et al.
WO 9422835, Oct. 13, 1994, Wayne, M. G., et al.
EP 632016, Jan. 4, 1995, Brewster, A. G., et al.
EP 632019, Jan. 4, 1995, Brown, G., Shute, R. E.
EP 632020, Jan. 4, 1995, Brown, G., Shute, R. E.
WO 95/00472, Jan. 5, 1995, Brewster, A. G., et al.
or
b) is a template which is defined analogously to the templates from the series of fibrinogen receptor antagonists and which is taken from the following patent applications:
Smithkline Beecham Corp.
WO 96/00574, Jan. 11, 1996, Cousins, R. D., et al.
Fujisawa Pharmaceutical Co.
WO 95/29907, Nov. 9, 1995, Kawai, Y., et al.
Eli Lilly
U.S. Pat. No. 5,488,058, Jan. 30, 1996, Palkowitz, A. D., et al.
U.S. Pat. No. 5,484,798, Jan. 16, 1996, Bryant, H. U., et al.;
or also is one of those templates which can be derived structurally from the templates which are described in the above patent applications, patent documents and publications;

F is defined like D;

G is 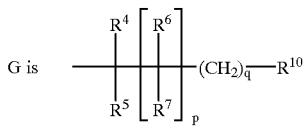

$R^2$ and $R^3$ are, independently of each other, H, $(C_1-C_{10})$-alkyl, which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl, $(C_1-C_8)$-alkyl, $R^8OC(O)R^9$, $R^8R^8NC(O)R^9$ or $R^8C(O)R^9$;

$R^4$, $R^5$, $R^6$ and $R^7$ are, independently of each other, H, fluorine, OH, $(C_1-C_8)$-alkyl, $(C_3-C_{14})$-cycloalkyl, $(C_3-C_{14})$-cycloalkyl-$(C_1-C_8)$-alkyl, or $R^8OR^9$, $R^8SR^9$, $R^8CO_2R^9$, $R^8OC(O)R^9$, $R^8$—$C_5-C_{14}$)-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is H, $(C_1-C_8)$-alkyl, $(C_3-C_{14})$-cycloalkyl, $(C_3-C_{14})$-cycloalkyl-$(C_1-C_8)$-alkyl, $(C_5-C_{14})$-aryl or $(C_5-C_{14})$-aryl-$(C_1-C_8)$-alkyl, where the alkyl radicals can be substituted, once or more than once, by fluorine;

$R^9$ is a direct linkage or $(C_1-C_8)$-alkanediyl;

$R^{10}$ is $C(O)R^{11}$, $C(S)_nR^{11}$, $S(O)R^{11}$, $P(O)(R^{11})_n$, or a four-membered to eight-membered, saturated or unsaturated heterocycle which contains 1, 2, 3 or 4 heteroatoms from the group N, O and S, such as tetrazolyl, imidazolyl, pyrazolyl, oxazolyl or thiadiazolyl;

$R^{11}$ is OH, $(C_1-C_8)$-alkoxy, $(C_5-C_{14})$-aryl-$(C_1-C_8)$-alkoxy, $(C_5-C_{14})$-aryloxy, $(C_1-C_8)$-alkylcarbonyloxy-$(C_1-C_4)$-alkoxy, $(C_5-C_{14})$-aryl-$(C_1-C_8)$-alkylcarbonyloxy-$(C_1-C_6)$-alkoxy, $NH_2$, mono- or di-$((C_1-C_8)$-alkyl)-amino, $(C_5-C_{14})$-aryl-$(C_1-C_8)$-alkylamino, $(C_1-C_8)$-dialkylaminocarbonylmethyloxy, $(C_5-C_{14})$-aryl-$(C_1-C_8)$-dialkylaminocarbonylmethyloxy or $(C_5-C_{14})$-arylamino or the radical of an L-amino acid or D-amino acid;

$R^{12}$, $R^{13}$, $R^{14}$ and $R^{15}$ are, independently of each other, H, $(C_1-C_{10})$-alkyl which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl$(C_1-C_8)$-alkyl, $H_2N$, $R^8ONR^9$, $R^8OR^9$, $R^9OC(O)R^9$, $R^8R^8NR^9$, $R^8$—$C_5-C_{14}$)-aryl-$R^9$, HO—

$(C_1-C_8)$-alkyl-N(R$^2$)R$^9$, R$^8$N(R$^2$)C(O)R$^9$, R$^8$C(O)N (R$^2$)R$^9$, R$^8$C(O)R$^9$, R$^2$R$^3$N—C(=NR$^2$)—NR$^2$, R$^2$R$^3$N—C(=NR$^2$), =O, or =S;
where two adjacent substituents from R$^{12}$ to R$^{15}$ can also together be —OCH$_2$O—, —OCH$_2$CH$_2$O— or —OC(CH$_3$)$_2$O—;
  y is NR$^2$, O or S;
  n is 1 or 2;
  p and q are, independently of each other, 0 or 1;
in all their stereoisomeric forms and mixtures thereof in all proportions, and their physiologically tolerated salts,
  with compounds being excepted in which E
    a) is a 6-membered aromatic ring system which can contain up to 4 N atoms and which can be substituted by from 1 to 4 identical or different arbitrary substituents, or
    b) is 4-methyl-3-oxo-2,3,4,5-tetrahydro-1-H-1,4-benzodiazepine.

A template from the series of fibrinogen receptor antagonists is understood to mean the central part of the molecular structure (of a fibrinogen receptor antagonist) to which, in the case of the fibrinogen receptor antagonists, a basic group and an acidic group are linked by way of spacers, with the basic and/or acidic group being present in protected form (prodrug) where appropriate.

In the fibrinogen receptor antagonists, the basic group is generally an N-containing group, such as amidine or guanidine, while the acidic group is generally a carboxyl function, with it being possible for the basic group and the acidic group to be present in each case in protected form.

A fibrinogen receptor antagonist is an active compound which inhibits the binding of fibrinogen to the blood platelet receptor GPIIbIIIa.

A fibrinogen receptor antagonist comprises a central part (template) to which a basic group and an acidic group are linked by way of spacers, with the basic group and/or acidic group being present in protected form (prodrug), where appropriate.

Alkyl radicals may be straight-chain or branched. This also applies if they carry substituents or appear as the substituents of other radicals, for example in alkoxy, alkoxycarbonyl or aralkyl radicals. Examples of suitable $(C_1-C_{10})$-alkyl radicals are: methyl, ethyl, propyl, butyl, pentyl, hexyl, heptyl, octyl, decyl, isopropyl, isopentyl, neopentyl, isohexyl, 3-methylpentyl, 2,3,5-trimethylhexyl, sec-butyl and tert-pentyl. Preferred alkyl radicals are methyl, ethyl, propyl, isopropyl, butyl, isobutyl, sec-butyl and tert-butyl.

Alkenyl and alkynyl radicals may also be straight-chain or branched. Examples of alkenyl radicals are vinyl, 1-propenyl, allyl, butenyl and 3-methyl-2-butenyl, while examples of alkynyl radicals are ethynyl, 1-propynyl or propargyl.

Cycloalkyl radicals may be monocyclic or polycyclic, e.g. bicyclic or tricyclic. Examples of monocyclic cycloalkyl radicals are cyclopropyl, cyclobutyl, cyclopentyl, cyclohexyl, cycloheptyl, cyclooctyl and cyclododecyl which, however, can also be substituted by, for example, $(C_1-C_4)$-alkyl. 4-Methylcyclohexyl and 2,3-dimethylcyclopentyl may be mentioned as examples of substituted cycloalkyl radicals.

Cyclodecane and cyclododecane are examples of parent substances of the monocyclic $(C_{10}-C_{14})$-cycloalkyl radicals in R$^4$, R$^5$, R$^6$ and R$^7$.

Bicyclic and tricyclic cycloalkyl radicals may be unsubstituted or substituted, in any suitable position, by one or more oxo groups and/or one or more identical or different $(C_1-C_4)$-alkyl groups, e.g. methyl groups or isopropyl groups, preferably methyl groups. The free bond of the bicyclic or tricyclic radical can be located in any position in the molecule; the radical can consequently be bonded via a bridgehead atom or via an atom in a bridge. The free bond can also be located in any stereochemical position, for example in an exo position or an endo position.

An example of a bicyclic ring system is decalin (decahydronaphthalene), while an example of a system substituted by an oxo group is 2-decanone.

Examples of parent substances of bicyclic ring systems are norbornane (=bicyclo[2.2.1]heptane), bicyclo[2.2.2]octane and bicyclo[3.2.1]octane. An example of a system which is substituted by an oxo group is camphor (=1,7,7-trimethyl-2-oxobicyclo[2.2.1]heptane).

Examples of parent substances of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Examples of parent substances of tricyclic $(C_{10}-C_{14})$-cycloalkyl radicals in R$^4$, R$^5$, R$^6$ and R$^7$ are twistane (=tricyclo[4.4.0.0.$^{3,8}$]decane, adamantane (=tricyclo[3.3.1.1.$^{3,7}$]nonane), tricyclo[5.3.2.0$^{4,9}$]dodecane, tricyclo[5.4.0.0$^{2,9}$]undecane or tricyclo[5.5.1.0$^{3,11}$]tridecane.

Halogen is fluorine, chlorine, bromine or iodine.

Examples of 6-membered aromatic ring systems are phenyl, pyridyl, pyridazinyl, pyrimidinyl, pyrazinyl, 1,3,5-triazinyl, 1,2,4-triazinyl, 1,2,3-triazinyl and tetrazinyl.

Aryl is, for example, phenyl, naphthyl, biphenylyl, anthryl or fluoroenyl, with 1-naphthyl, 2-naphthyl and, in particular, phenyl being preferred. Aryl radicals, in particular phenyl radicals, may be substituted, once or more than once, preferably once, twice or three times, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, —OCH$_2$CH$_2$O—, —OC(CH$_3$)$_2$O—, cyano, hydroxycarbonyl, aminocarbonyl, $(C_1-C_4)$-alkoxycarbonyl, phenyl, phenoxy, benzyl, benzyloxy, (R$^{17}$O)$_2$P(O), (R$^{17}$O)$_2$P(O)—O— or tetrazolyl, where R$^{17}$ is H, $(C_1-C_{10})$-alkyl, $(C_6-C_{14})$-aryl or $(C_6-C_{14})$-aryl-$(C_1-C_8)$-alkyl.

In monosubstituted phenyl radicals, the substituent can be located in the 2, 3 or 4 position, with the 3 and 4 positions being preferred. If phenyl is substituted twice, the substituents can be in the 1, 2 or 1, 3 or 1,4 positions relative to each other. The two substituents in phenyl radicals which are substituted twice are preferably arranged in the 3 and 4 position, based on the linkage site.

Aryl groups can also be monocyclic or polycyclic aromatic ring systems in which from 1 to 5 carbon atoms can be replaced by from 1 to 5 heteroatoms, such as 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or β-carbolinyl, or a benzo-fused, cyclopenta-, cyclohexa- or cyclohepta-fused derivative of these radicals. These heterocycles can be substituted by the same substituents as the abovementioned carbocyclic aryl systems.

Of these aryl groups, preference is given to monocyclic or bicyclic aromatic ring systems which have from 1 to 3 heteroatoms from the group N, O and S and which can be substituted by from 1 to 3 substituents selected from the group consisting of $(C_1-C_6)$-alkyl, $(C_1-C_6)$-alkoxy, F, Cl, $NO_2$, $NH_2$, $CF_3$, OH, $(C_1-C_4)$-alkoxycarbonyl, phenyl, phenoxy, benzyloxy or benzyl.

In this context, particular preference is given to monocyclic or bicyclic aromatic 5-membered to 10-membered ring systems which have from 1 to 3 heteroatoms from the group N, O and S and which can be substituted by from 1 to 2 substituents from the group consisting of $(C_1-C_4)$-alkyl, $(C_1-C_4)$-alkoxy, phenyl, phenoxy, benzyl or benzyloxy.

L- or D-amino acids can be natural or unnatural amino acids. α-Amino acids are preferred. The following may be mentioned by way of example (cf. Houben-Weyl, Methoden der organischen Chemie [Methods of Organic Chemistry], Volume XV/1 and 2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)₂, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Om, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid and 2-(p-chlorophenyl) aminoacetic acid;

and also:
pyrrolidine-2-carboxylic acid; piperidine-2-carboxylic acid; 1,2,3,4-tetra-hydroisoquinoline-3-carboxylic acid; decahydroisoquinoline-3-carboxylic acid; octahydroindole-2-carboxylic acid; decahydroquinoline-2-carboxylic acid; octahydrocyclopentatblpyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid;

decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydmindole-2-carboxylic acid; tetrahydrothiazole-4-carboxylic acid; isoxazolidine-3-carboxylic acid; pyrazolidine-3-carboxylic acid and hydroxypyrrolidine-2-carboxylic acid, all of which can optionally be substituted (see the following formulae):

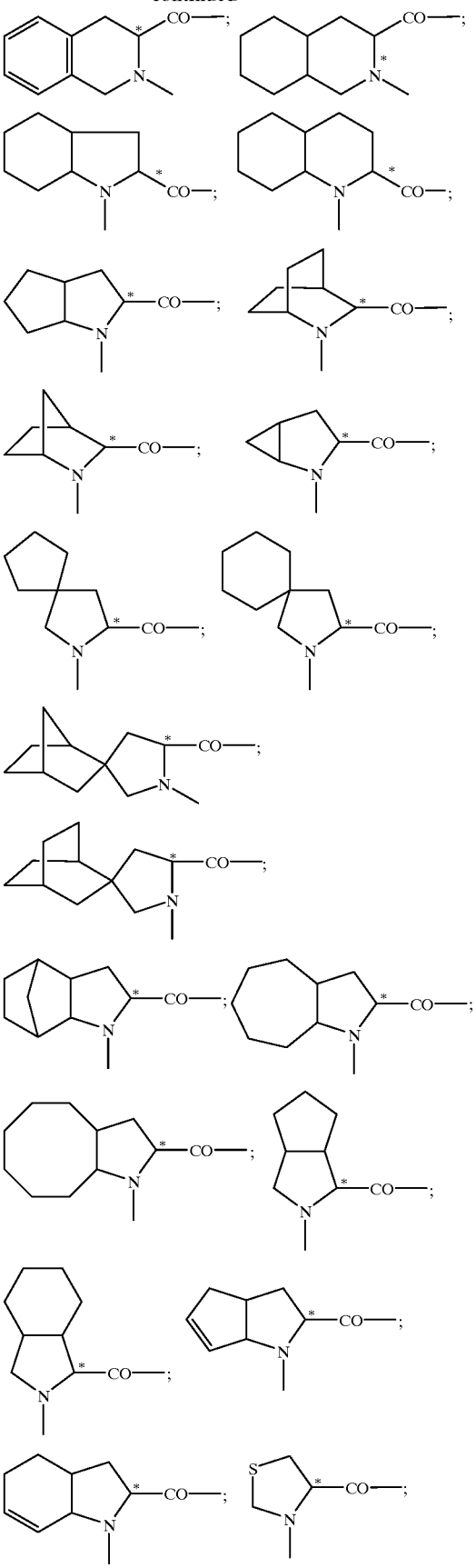

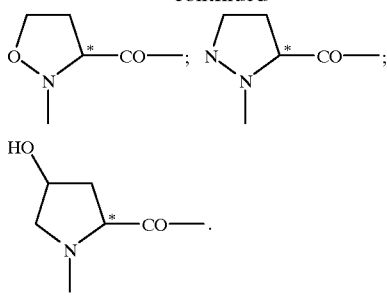

The heterocycles on which the abovementioned radicals are based are disclosed, for example, in U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

In addition, the amino acids can also be present as esters or amides, such as methyl esters, ethyl esters, isopropyl esters, isobutyl esters, tert-butyl esters, benzyl esters, unsubstituted amide, ethylamide, semicarbazide or ω-amino-$(C_2-C_8)$-alkylamide.

Functional groups of the amino acids may be present in protected form. Suitable protecting groups, such as urethane protecting groups, carboxyl protecting groups and side-chain protecting groups, are described in Hubbuch, Kontakte (Merck) 1979, No. 3, pages 14 to 23 and in Büllesbach, Kontakte (Merck) 1980, No. 1, pages 23 to 35. Those which may, in particular, be mentioned are: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-butyl, OBzl, ONbzl, OMbzl, Bzl, Mob, Pic, Trt.

Physiologically tolerated salts of the compounds of the formula I are, in particular, pharmaceutically utilizable or nontoxic salts. Such salts are formed, for example, from compounds of the formula I which contain acidic groups, e.g. carboxyl, with alkali metals or alkaline earth metals, such as Na, K, Mg and Ca, and also with physiologically tolerated organic amines, such as triethylamine, ethanolamine or tris-2-hydroxyethyl)amine. Compounds of the formula I which contain basic groups, e.g. an amino group, an amidino group or a guanidino group, form salts with inorganic acids, such as hydrochloric acid, sulfuric acid or phosphoric acid, and with organic carboxylic acids or sulfonic acids, such as acetic acid, citric acid, benzoic add, maleic acid, fumaric add, tartaric acid, lactic acid, methanesulfonic acid or p-toluenesulfonic acid.

The novel compounds of the formula I may contain optically active carbon atoms, which, independently of each other, can have R or S configurations, and they consequently may be present in the form of pure enantiomers or pure diastereomers or in the form of enantiomeric mixtures or diastereomeric mixtures. The present invention relates both to pure enantiomers and enantiomeric mixtures in all proportions and to diastereomers and diastereomeric mixtures in all proportions.

The novel compounds of the formula I may be present, independently of each other, as E/Z isomeric mixtures. The present invention relates both to pure E and Z isomers and to E/Z isomeric mixtures. Diastereomers, including E/Z isomers, can be separated into the individual isomers by means of chromatography. Racemates can be separated into the two enantiomers either by means of chromatography on chiral phases or by means of racemate resolution.

In addition to this, the novel compounds of the formula I may contain mobile hydrogen atoms, that is they may be present in different tautomeric forms. The present invention also relates to all these tautomers.

The present invention moreover includes all solvates of compounds of the formulae I and Ia, for example hydrates or adducts with alcohols, and also derivatives of the compounds of the formulae I and Ia, for example esters, prodrugs and metabolites, which act like the compounds of the formulae I and Ia.

Preference is given to compounds of the formula I which are selective vitronectin receptor antagonists, particularly in relation to the fibrinogen receptor, i.e. which are stronger inhibitors of the vitronectin receptor than of the fibrinogen receptor.

Preference is given, in particular, to compounds of the formula I which are selective vitronectin receptor antagonists and in which the distance between $R^{10}$ and the first N atom in A is from 12 to 13 covalent bonds along the shortest route between these atoms, as depicted below, by way of example, for

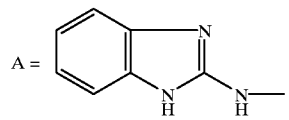

and $R^{10}$=COOH:

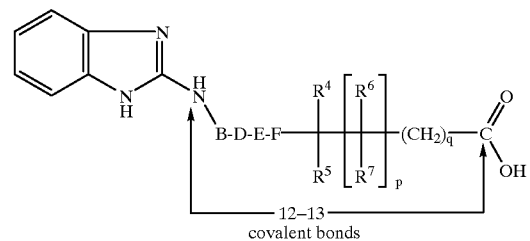

Preference is also given to compounds of the formula I in which at least one radical from the group $R^4$, $R^5$, $R^6$ and $R^7$ is a lipophilic radical.

Examples of lipophilic radicals in the group $R^4$, $R^5$, $R^6$ and $R^7$ are neopentyl, cyclohexyl, adamantyl, cyclohexyl-$(C_1-C_8)$-alkyl, adamantyl-$(C_1-C_8)$-alkyl, phenyl, naphthyl, phenyl-$(C_1-C_8)$-alkyl, naphthyl-$(C_1-C_8)$-alkyl, cyclohexylmethylcarbonylamino, 1-adamantylmethyloxycarbonylamino or benzyloxycarbonylamino, or, generally, radicals in which $R^8$ is, for example, neopentyl, cyclohexyl, adamantyl, cyclohexyl-$(C_1-C_8)$-alkyl, adamantyl-$(C_1-C_8)$-alkyl, phenyl, naphthyl or phenyl-$(C_1-C_8)$-alkyl.

Preference is furthermore given to compounds of the formula I in which:

A is the radical

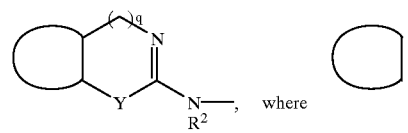

is a 5-membered to 10-membered monocyclic or polycyclic, aromatic or nonaromatic ring system which can contain from 1 to 4 heteroatoms from the group consisting of N, O and S and which can optionally be substituted, once or more than once, by $R^{12}$, $R^{13}$, $R^{14}$ and $R^{15}$;

B is a direct linkage, $(C_1-C_6)$-alkanediyl, $(C_5-C_8)$-arylene, $(C_3-C_8)$-cycloalkylene, —C≡C—, —$NR^2$—, —$NR^2$—C(O)—, —$NR^2$—C(O)—$NR^2$—, —$NR^2$—S(O)—, —$NR^2$—S(O)$_2$—, —O— or —$CR^2$=$CR^3$— which can in each case be substituted, once or twice, by $(C_1-C_6)$-alkyl;

D is a direct linkage, $(C_1-C_8)$-alkanediyl, $(C_5-C_8)$-arylene, —O—, $NR^2$—, —CO—$NR^2$—, —$NR^2$—CO—, —$NR^2$—C(O)—$NR^2$—, —OC(O)—, —C(O)O—, —S(O)$_2$—, —S(O)$_2$—$NR^2$—, —$NR^2$—S(O)$_2$—, —S—, —$CR^2$=$CR^3$— or —C≡C— which can in each case be substituted, once or twice, by $(C_1-C_8)$-alkyl, —$CR^2$=$CR^3$— or $(C_5-C_6)$-aryl, with it not being possible for D to be —CO—$NR^2$—, —C(O)O—, —SO$_2$— or —S(O)$_2$—$NR^2$— when B is a direct linkage;

E is a template which is selected from the fibrinogen receptor antagonist group and which is taken from:
U.S. Pat. No. 5,250,679, Oct. 5, 1993, Blackburn, B. K. et al.
U.S. Pat. No. 5,403,836, Apr. 4, 1995, Blackburn, B. K. et al.
U.S. Pat. No. 5,565,449, Oct. 15, 1996, Blackburn, B. K. et al.
WO 93108174, Oct. 15, 1991, Blackburn, B. K. et al.
WO 95104057, Feb. 9, 1995, Blackburn, B. K. et al.
EP 0 655 439, Nov. 9, 1994, Denney, M. L. et al.
WO 94/18981, Sep. 1, 1994, Claremon, D. A. et al.
WO 94/08962, Apr. 28, 1994, Harmann, G. D. et al.
EP 0 668 278, Feb. 14, 1995, Juraszyk, H. et al.
WO 94/12478, Jun. 9, 1994, Keenan, E. Mc. C. et al.
F is defined like D;

G is 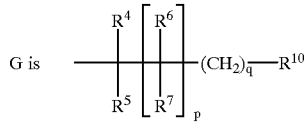

$R^2$ and $R^3$ are, independently of each other, H, $(C_1-C_{10})$-alkyl, which is optionally substituted, once or more than once, by fluorine, $(C_3-C_8)$-cycloalkyl, $(C_3-C_8)$-cycloalkyl-$C_1-C_6$-alkyl, $(C_5-C_{12})$-aryl, $(C_5-C_{12})$-aryl-$C_1-C_6$-alkyl, $R^8OC(O)R^9$, $R^8R^8NC(O)R^9$ or $R^8C(O)R^9$;

$R^4$, $R^5$, $R^6$ and $R^7$ are, independently of each other, H, fluorine, OH, $(C_1-C_8)$-alkyl, $(C_5-C_{14})$-cydoalkyl, $(C_5-C_{14})$-cycloalkyl-$C_1-C_8$-alkyl, or $R^8OR^9$, $R^8SR^9$, $R^8CO_2R^9$, $R^8OC(O)R^9$, $R^8$—$(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is H, $(C_1-C_6)$-alkyl, $(C_5-C_{14})$-cycloalkyl, $(C_5-C_{14})$-cycloalkyl-$(C_1-C_6)$-alkyl, $(C_5-C_{12})$-aryl or $(C_5-C_{12})$-aryl-$(C_1-C_6)$-alkyl, where the alkyl radicals can be substituted, once or more than once, by fluorine;

$R^9$ is a direct linkage or $(C_1-C_6)$-alkanediyl;

$R^{10}$ is $C(O)R^{11}$, $C(S)R^{11}$, $S(O)_nR^{11}$, $P(O)(R^{11})_n$ or a four-membered to eight-membered, saturated or unsaturated heterocycle which contains 1, 2, 3 or 4 heteroatoms from the group N, O and S;

$R^{11}$ is OH, $(C_1-C_6)$-alkoxy, $(C_5-C_{12})$-aryl-$(C_1-C_6)$-alkoxy, $(C_5-C_{12})$-aryloxy, $(C_1-C_6)$-alkylcarbonyloxy-$(C_1-C_4)$-alkoxy, $(C_5-C_{12})$-aryl-$(C_1-C_6)$-alkylcarbonyloxy-$(C_1-C_6)$-alkoxy, $NH_2$, mono- or di-$((C_1-C_6)$-alkyl)-amino, $(C_5-C_{12})$-aryl-$(C_1-C_6)$-alkylamino, $(C_1-C_6)$-dialkylaminocarbonylmethyloxy;

$R^{12}$, $R^{13}$, $R^{14}$ and $R^{15}$ are, independently of each other, H, $(C_1-C_8)$-alkyl which is optionally substituted, once or more than once, by fluorine, $(C_3-C_8)$-cycloalkyl, $(C_3-C_8)$-cloalkyl-$(C_1-C_6)$-alkyl, $(C_5-C_{12})$-aryl, $(C_5-C_{12})$-aryl-$(C_1-C_6)$-alkyl, $H_2N$, $R^8ONR^9$, $R^8OR^9$, $R^8OC(O)R^9$, $R^8$—$C_5-C_{12}$)-aryl-$R^9$, $R^8R^8NR^9$, HO—$(C_1-C_8)$-alkyl-$N(R^2)R^9$, $R^8N(R^2)C(O)R^9$, $R^8C(O)N(R^2)R^9$, $R^8C(O)R^9$, $R^2R^3N$—C(=$NR^2$), $R^2R^3N$—C(=$NR^2$)—$NR^2$, =O or =S;

where two adjacent substituents from $R^{12}$ to $R^{15}$ can also together be —$OCH_2O$—, —$OCH_2CH_2O$— or —$OC(CH_3)_2O$—;

Y is $NR^2$, O or S;

n is 1 or 2;

p and q are, independently of each other, 0 or 1;

in all their stereoisomeric forms and mixtures thereof in all proportions, and their physiologically tolerated salts.

Particular preference is given to compounds of the formula I in which:

A is one of the radicals

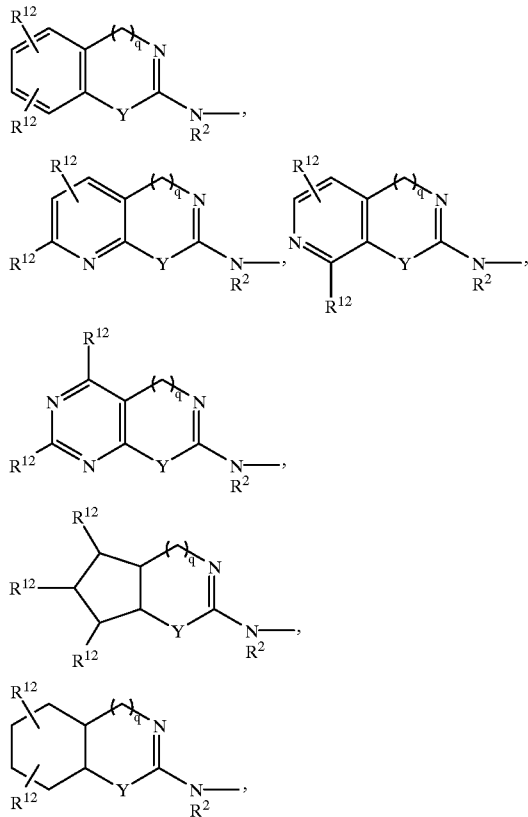

-continued

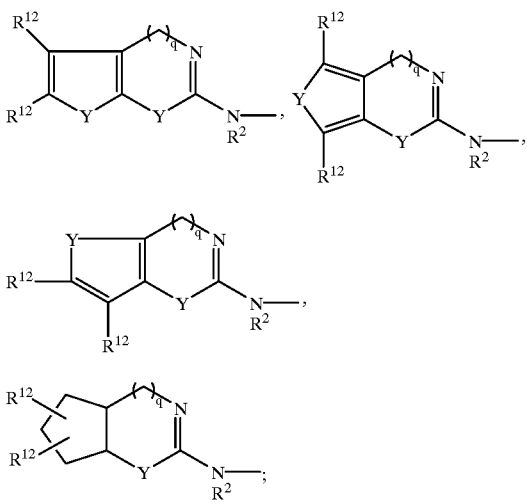

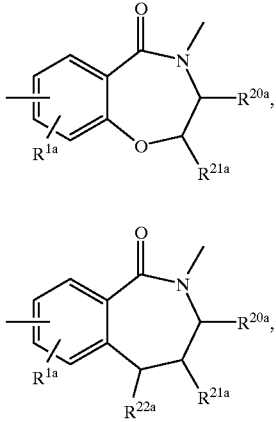

B is a direct linkage, $(C_1-C_6)$-alkanediyl, $(C_5-C_6)$-arylene, $(C_5-C_6)$-cycloalkylene, $-C\equiv C-$, $-NR^2-$, $-NR^2-C(O)-$, $-NR^2S(O)_2-$, $-O-$ or $-CR^2=CR^3-$, which can in each case be substituted, once or twice, by $(C_1-C_6)$-alkyl;

D is a direct linkage, $(C_1-C_6)$-alkanediyl, $(C_5-C_6)$-arylene, $-O-$, $-NR^2-$, $-NR^2-C(O)-$, $-C(O)NR^2-$, $-NR^2-C(O)-NR^2-$, $-OC(O)-$, $-S(O)_2-NR^2-$, $-NR^2-S(O)_2-$ or $-CR^2=CR^3-$ which can in each case be substituted, once or twice, by $(C_1-C_6)$-alkyl, with it not being possible for D to be $-C(O)NR^2-$ or $-S(O)_2-NR^2-$ when B is a direct linkage;

E a) is a template from WO 93108174, U.S. Pat. No. 5,250,679, U.S. Pat. No. 5,403,836 or U.S. Pat. No. 5,565,449, specifically:

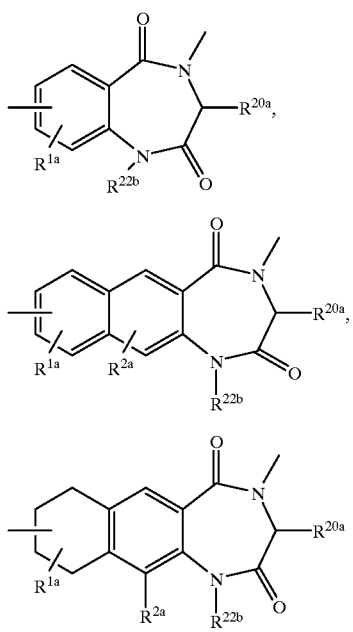

where $R^{1a}$, $R^{2a}$, $R^{20a}$, $R^{21a}$ and $R^{22a}$ are defined like $R^1$, $R^2$, $R^{20}$, $R^{21}$ and $R^{22}$ in U.S. Pat. No. 5,403,836, column 249, lines 9–22; and column 252, line 66 to column 253, line 68, and consequently:

$R^{1a}$ and $R^{2a}$ are, independently of each other, from one to three groups from the series consisting of hydrogen, halogen, cyano, carboxamido, carbamoyloxy, formyloxy, formyl, azido, nitro, ureido, thioureido, hydroxyl, mercapto or sulfonamido, or an optionally substituted radical from the group consisting of $C_1-C_{12}$-alkyl, $C_2-C_{12}$-alkenyl, $C_3-C_{12}$-alkynyl, $C_3-C_{12}$-cycloalkyl, $C_6-C_{14}$-aryl, $C_6-C_{10}$-aryl-$C_1-C_8$-alkyl, $C_1-C_{12}$-alkyloxy-$C_6-C_{14}$-aryloxy and $C_1-C_{12}$-acylamino, where the substituents are a radical from the group consisting of halogen, cyano, azido, nitro, hydroxyl, mercapto, sulfonamido, ureido, thioureido, carboxamido, carbamoyloxy, formyloxy, formyl, $C_1-C_4$-alkoxy, phenyl and phenoxy;

$R^{20a}$ is hydrogen, halogen (fluorine, chlorine, bromine or iodine), $C_1-C_4$-alkoxy, $C_1-C_4$-alkyl, phenyl, benzyl or halogen-$C_1-C_4$-alkyl, $R^{21a}$ and $R^{22a}$ are, independently of each other,
1. hydrogen
2. $(C_1-C_{12})$-alkyl
3. $(C_6-C_{14})$-aryl,
4. $(C_3-C_{14})$-cycloalkyl,
5. $(C_1-C_{12})$-alkyl-$C_6-C_{14})$-aryl,
6. $(C_1-C_{12})$-alkyl-$C_3-C_{14})$-cycloalkyl, where the radicals defined under 2. to 6. can be substituted by one or more radicals from the group consisting of
halogen (fluorine, chlorine, bromine or iodine); nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; $COR^{24a}$ or $CONR^{25}R^{26}$; where
$R^{24a}$ is a radical from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy, such as acetylaminoethoxy, nicotinoylaminoethoxy, succinamidoethoxy or pivaloylethoxy; or $C_6-C_{12}$-aryl-$C_1-C_8$-alkoxy, where the aryl group can be optionally substituted by from one to three radicals selected from the group consisting of nitro, halogen, $C_1-C_4$-alkoxy, amino, hydroxyl, hydroxy-$C_2-C_8$-alkoxy or dihydroxy-$C_3-C_8$-alkoxy;
$R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or $R^{25}$ and $R^{26}$ together form a trimethylene, tetramethylene, pentamethylene or 3-oxopentamethylene radical;

7. $Q^2$—$L^3$, where
   $Q^2$ is hydrogen or $Q^1$; and
   $L^3$ is a chemical bond, $L^1$ or $L^2$;
      $Q^1$ is a substituted or unsubstituted, positively charged, nitrogen-containing radical,
      $L^1$ is a divalent radical which contains from 3 to 9 methylene groups, where from one to all the methylene groups can be replaced with one or more alkene groups, alkyne groups, aryl groups or functional groups containing heteroatoms from the group consisting of N, O or S, and
      $L^2$ is an optionally substituted, divalent radical;
where preferred radicals for $Q^1$, $L^1$ and $L^2$ are those radicals as described in U.S. Pat. No. 5,403,836 in column 249, line 27 to column 251, line 6 ($Q^1$), column 251, line 7 to column 252, line 18 ($L^1$) and column 252, lines 19–45 ($L^2$);

and $R^{22b}$ is defined like $R^{22}$ in U.S. Pat. No. 5,565,449, column 296, line 38 to column 297, line 38, and is:
1. hydrogen
2. $(C_1-C_{12})$-alkyl
3. $(C_6-C_{14})$-aryl,
4. $(C_3-C_{14})$-cycloalkyl,
5. $(C_1-C_{12})$-alkyl-$(C_6-C_{14})$-aryl,
6. $(C_1-C_{12})$-alkyl-$(C_3-C_{14})$-cycloalkyl, where the radicals defined under 2. to 6. can be substituted by one or more radicals from the group consisting of halogen (fluorine, chlorine, bromine or iodine); nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_{3-14}$-cycloalkyl; $COR^{24a}$ or $CONR^{25}R^{26}$; where
   $R^{24a}$ is a radical from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy, such as acetylaminoethoxy, nicotinoylaminoethoxy, succinamidoethoxy or pivaloylethoxy; or $C_6-C_{12}$-aryl-$C_1-C_8$-alkoxy, where the aryl group can optionally be substituted by from one to three radicals selected from the group consisting of nitro, halogen, $C_1-C_4$-alkoxy, amino, hydroxyl, hydroxy-$C_2-C_8$-alkoxy or dihydroxy-$C_3-C_8$-alkoxy;
   $R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or
   $R^{25}$ and $R^{26}$ together form a trimethylene, tetramethylene, pentamethylene or 3oxopentamethylene radical;

7. $Q^2$—$L^3$ where
   $Q^2$ is hydrogen or $Q^1$; and
   $L^3$ is a chemical bond, $L^1$ or $L^2$;
      $Q^1$ is a substituted or unsubstituted, positively charged, nitrogen-ontaining radical,
      $L^1$ is a divalent radical which contains from 3 to 9 methylene groups, where from one to all the methylene groups can be replaced with one or more alkene radicals, alkyne radicals, aryl radicals or functional groups containing heteroatoms from the group consisting of N, O or S, and
      $L^2$ is an optionally substituted, divalent radical;
where preferred radicals for $Q^1$, $L^1$ and $L^2$ are those radicals as described in U.S. Pat. No. 5,403,836 in column 289, line 9 to column 293, line 17 ($Q^1$), column 293, line 18 to column 295, line 28 ($L^1$) and column 295, line 29 to column 296, line 11 ($L^2$);

or b) is a template from WO 95/04057, specifically:

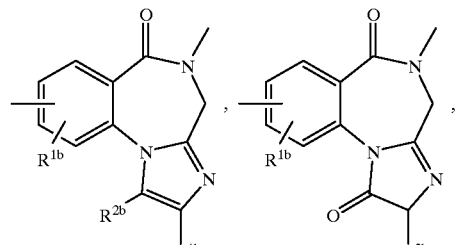

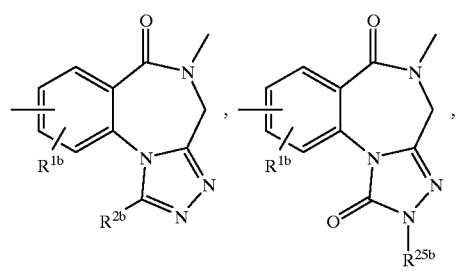

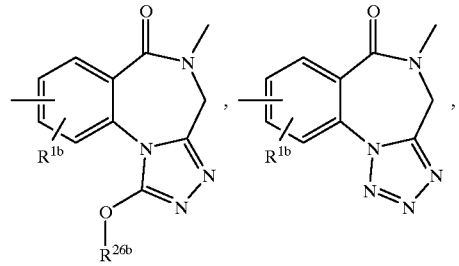

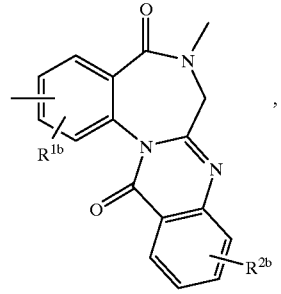

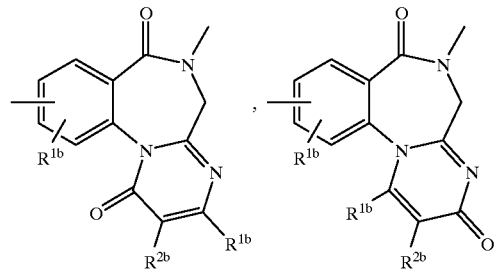

-continued

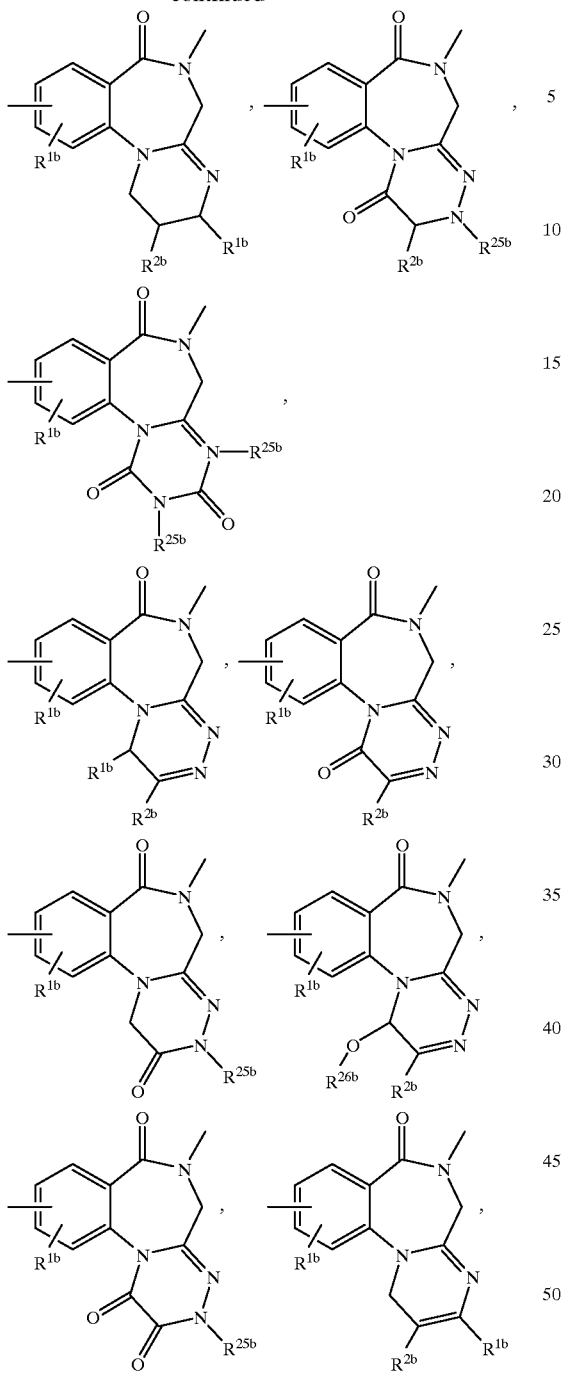

where $R^{1b}$ and $R^{2b}$ are defined like $R^1$ and $R^2$ in U.S. Pat. No. 5,403,836, column 249, lines 9–22; and:

$R^{1b}$ and $R^{2b}$ are, independently of each other, from one to three groups from the series consisting of hydrogen, halogen, cyano, carboxamido, carbamoyloxy, formyloxy, formyl, azido, nitro, ureido, thioureido, hydroxyl, mercapto or sulfonamido, or an optionally substituted radical from the group consisting of $C_1$–$C_{12}$-alkyl, $C_2$–$C_{12}$-alkenyl, $C_3$–$C_{12}$-alkynyl, $C_3$–$C_{12}$-cycloalkyl, $C_6$–$C_{14}$-aryl, $C_6$–$C_{10}$-aryl-$C_1$–$C_8$-alkyl, $C_1$–$C_{12}$-lkyloxy,$C_6$–$C_{14}$-aryloxy and $C_{12}$-acacylamino, where the substituents are a radical from the group consisting of halogen, cyano, azido, nitro, hydroxyl, mercapto, sulfonamido, ureido, thioureido, carboxamido, carbamoyloxy, formyloxy, formyl, $C_1$–$C_4$-alkoxy, phenyl and phenoxy; and $R^{25b}$ and $R^{26b}$ are defined like $R^{25}$ and $R^{26}$ in U.S. Pat. No. 5,565,449 and:

$R^{25b}$ and $R^{26b}$ are, independently of each other, hydrogen, $C_1$–$C_{10}$-alkyl, $C_3$–$C_{10}$-alkenyl, $C_6$–$C_{14}$-aryl or $C_1$–$C_6$-alkyl-$C_6$–$C_{10}$-aryl, or $R^{25b}$ and $R^{26b}$ together form a trimethylene, tetramethylene, pentamethylene or 3-oxopentamethylene radical;

or c)

is a template from EP-A 0 655 439, specifically

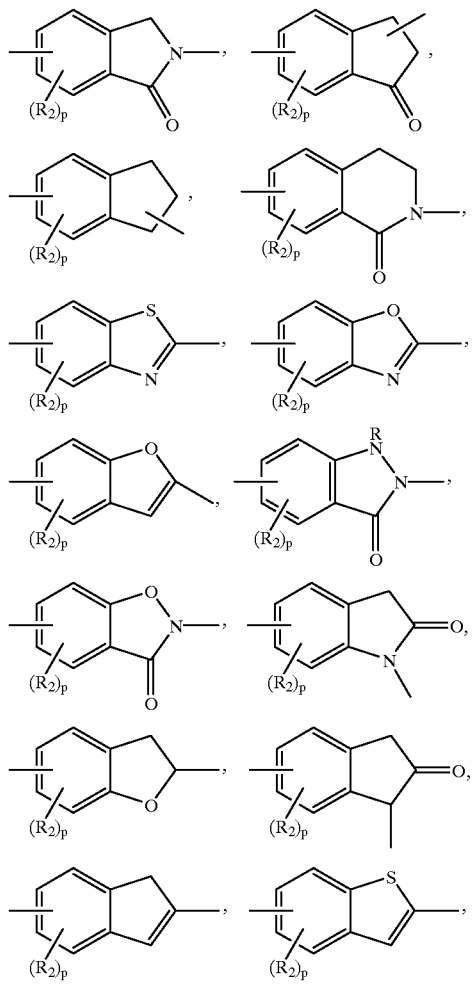

where $(R_2)_p$ is bonded to one or more carbon atoms of the 6-membered ring and is, independently of each other, a radical from the group consisting of H, alkyl, halogen-substituted alkyl, hydroxyalkyl, alkenyl, alkynyl, cycloalkyl, aryl, aryloxy, aralkyl, hydroxyl, alkoxy, aralkoxy, carbamyl, amino, substituted amino, acyl, cyano, halogen, nitro and sulfo;

R is $(C_1$–$C_4)$-alkyl p is an integer from 1 to 3, or d)

is a template from WO 94/12478, specifically

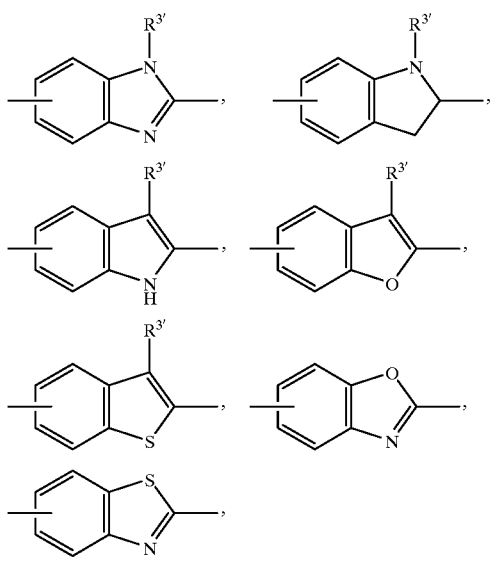

where R³' is hydrogen, (C₁–C₆)-alkyl or aryl-C₁–C₆-alkyl, or e) is a template from WO94/18981, specifically 1.
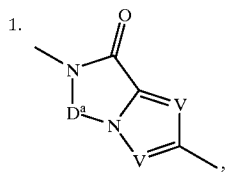

in which V is CR$^{7a}$ or N, and
D$^a$ is CH₂, CH₂—CH₂, CH₂C(R$^{7a}$)₂CH₂ or

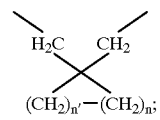

2.
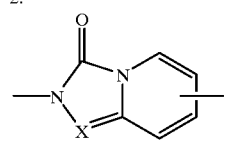

in which X is CR$^{3a}$ or N,
where R$^{3a}$ is CN, C(O)N(R$^{7a}$)R$^{8a}$,

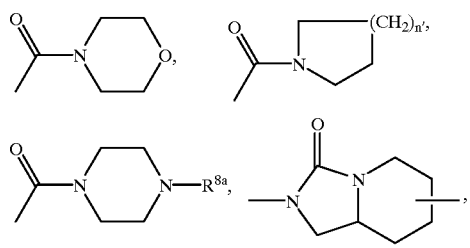

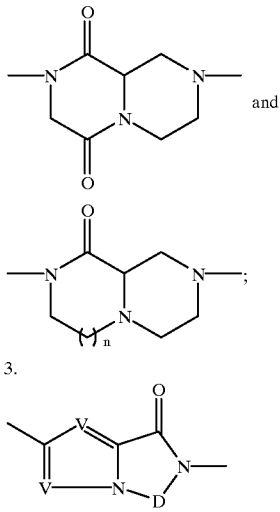

3.

in which V is CR$^{7a}$ or N, and
D$^a$ is CH₂, CH₂—CH₂, CH₂C(R$^{7a}$)₂CH₂ or

4.
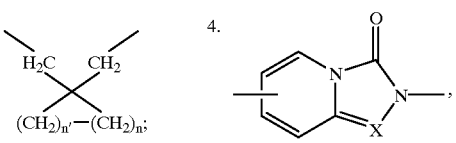

in which X is CR or N, in which
R$^{3a}$ is CN, C(O)N(R$^{7a}$)R$^{8a}$,

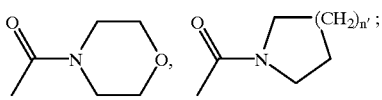

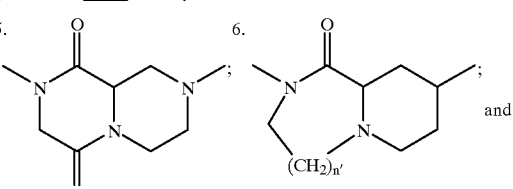

7.
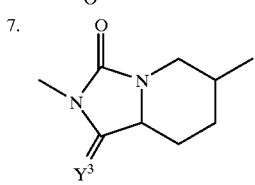

where Y³ is O or H₂, and

R$^{7a}$ is hydrogen; C₁–C₄-alkyl which is optionally substituted by OH or (C₁–C₄)-alkoxcy; C₂–C₆-alkenyl which is optionally substituted by (C₁–C₄)-alkoxy; or OH (C₁–C₄)-alkylaryl; or aryl which is optionally substituted by identical or different radicals from the group consisting of halogen, (C₁–C₄)-alkoxy, hydroxyl or (C₁–C₄)-alkyl, R$^{8a}$ is hydrogen or C₁–C₄-alkyl, n is an integer from 0 to 7, and n' is an integer from 0 to 3;

or f) is a template from EP-A 0531 883, specifically

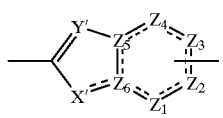

where:
- X' is an oxygen, sulfur or nitrogen atom or an —NR$^{2b}$- group, where
  R$^{2b}$ is a hydrogen atom, a straight-chain or branched alkyl group having from 1 to 15 carbon atoms, a straight-chain or branched alkenyl or alkynyl group having in each case from 3 to 10 carbon atoms, where the double bond or triple bond cannot connect directly to the nitrogen atom, a cycloalkyl or cycloalkylalkyl group having in each case from 3 to 7 carbon atoms in the cycloalkyl moiety, an aryl group, an alkyl group having from 2 to 6 carbon atoms which is substituted, from the β position to the nitrogen atom of the —NR$^{2b}$-group onwards, by an R$^{3b}$O, (R$^{3b}$)$_2$N—, R$^{4b}$CO—NR$^{3b}$—, alkylsulfonyl—NR$^{3b}$—, arylsulfonyl-NR$^{3b}$—, alkylsulfenyl, alkylsulfinyl, alkylsulfonyl or R$^{5b}$ group, or an alkyl group having from 1 to 6 carbon atoms which is substituted by one or two aryl groups, R$^{6b}$OCO—, (R$^{3b}$)$_2$NCO—, R$^{5b}$—CO—, R$^{3b}$O—CO-alkylene-NR$_3$—CO—, (R$^{3b}$)$_2$NCO-alkylene—NR$^{3b}$—OC or R$^{5b}$CO-alkylene-NR$^{5b}$—CO-group, in which R$^{3b}$ and R$^{5b}$ are defined as indicated below and R$^{6b}$ is a hydrogen atom, an alkyl group having from 1 to 6 carbon atoms, a cycloalkyl group having from 5 to 7 carbon atoms or an aralkyl group,
- Y' is an NO-group, a nitrogen atom or a methine group which is optionally substituted by an alkyl group,
- Z$_1$, Z$_2$, Z$_3$ and Z$_4$, which can be identical or different, are methine groups, carbon atoms, imino groups or nitrogen atoms, where at least one of the radicals Z$_1$ to Z$_4$ has to contain a carbon-atom, and one or two methine groups which are adjacent to a nitrogen atom can in each case be replaced by carbonyl groups,
- Z$_5$ and Z$_6$ are in each case a carbon atom, or else one of the radicals Z$_5$ or Z$_6$ is a nitrogen atom and the other of the radicals Z$_5$ or Z$_6$ is a carbon atom,
- R$^{3b}$ is a hydrogen atom, an alkyl group having from 1 to 6 carbon atoms, or an aryl, aralkyl, carboxyalkyl or alkoxycarbonylalkyl group,
- R$^{4b}$ is a hydrogen atom, an alkyl or alkoxy group having in each case from 1 to 6 carbon atoms, or an aryl or aralkyl group having from 1 to 6 carbon atoms in the alkyl moiety, and
- R$^{5b}$ is an azetidino, pyrrolidino, hexamethylenimino or heptamethylenimino group or a piperidino group in which the methylene group in the 4 position can be replaced by an oxygen atom, by a sulfenyl, sulfinyl or sulfonyl group, or by an imino group which is substituted by an R$_3$, R$_4$CO—, alkylsulfonyl or arylsulfonyl group, where R$_3$ and R$_4$ are defined as mentioned above;
- F is a direct linkage, (C$_1$–C$_6$)-alkanediyl, —O—, —CO—NR$^2$—, —NR$^2$—CO—, —NR$^2$—C(O)—NR$^2$—, —OC(O)—, —C(O)O—, —CO—, —S(O)$_2$—, —S(O)$_2$—NR$^2$—, —NR$^2$—S(O)$_2$—, —CR$^2$=CR$^3$—, —C≡C— which can in each case be substituted, once or twice, by (C$_1$–C$_6$)-alkyl;

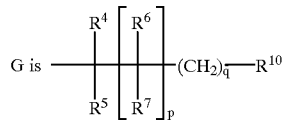

- R$^2$ and R$^3$ are, independently of each other, H, (C$_1$–C$_6$)-alkyl which is optionally substituted, once or more than once, by fluorine, (C$_5$–C$_6$)-cycloalkyl, (C$_5$–C$_6$)-cloalkyl-(C$_1$–C$_4$)-alkyl, (C$_5$–C$_{10}$)-aryl, (C$_5$–C$_{10}$)-aryl-(C$_1$–C$_4$)-alkyl, R$^8$OC(O)R$^9$, R$^8$R$^8$NC(O)R$^9$ or R$^8$C(O)R$^9$;
- R$^4$, R$^5$, R$^6$ and R$^7$ are, independently of each other, H, fluorine, OH, (C$_1$–C$_6$)-alkyl, (C$_5$–C$_{14}$)-cycloalkyl, (C$_5$–C$_{14}$)-cycloalkyl-(C$_1$–C$_6$)-alkyl, or R$^8$OR$^9$, R$^8$CO$_2$R$^9$, R$^8$OC(O)R$^9$, R$^8$—(C$_5$–C$_{10}$)-aryl-R$^9$, R$^8$NHR$^9$, R$^8$R$^8$NR$^9$, R$^8$NHC(O)OR$^9$, R$^8$S(O)$_n$NHR$^9$, R$^8$OC(O)NHR$^9$, R$^8$C(O)NHR$^9$, R$^8$C(O)R$^9$, R$^8$NHC(O)NHR$^9$, R$^8$NHS(O)$_n$NHR$^9$, R$^8$NHC(O)R$^9$ or R$^8$NHS(O)$_n$R$^9$, where at least one radical from the group R$^4$, R$^5$, R$^6$ and R$^7$ is a lipophilic radical, such as benzyloxycarbonylamino, cyclohexylmethylcarbonylamino etc.;
- R$^8$ is H, (C$_1$–C$_6$)-alkyl, (C$_5$–C$_{14}$)-cycloalkyl, (C$_5$–C$_{14}$)-cycloalkyl-C$_1$–C$_4$)-alkyl, (C$_5$–C$_{10}$)-aryl or (C$_5$–C$_{10}$)-aryl-C$_1$–C$_4$)-alkyl, where the alkyl radicals can be substituted by from 1 to 6 fluorine atoms;
- R$^9$ is a direct linkage or (C$_1$–C$_6$)-alkanediyl;
- R$^{10}$ is C(O)R$^{11}$;
- R$^{11}$ is OH, (C$_1$–C$_6$)-alkoxy, (C$_5$–C$_{10}$)-aryl-C$_1$–C$_6$)-alkoxy, (C$_5$–C$_{10}$)-aryloxy, (C$_1$–C$_6$)-alkylcarbonyloxy (C$_1$–C$_4$)-alkoxy, (C$_5$–C$_{10}$)-aryl-C$_1$–C$_4$)-alkylcarbonyloxy-C$_1$–C$_4$)-alkoxy, NH$_2$ or mono- or di-(C$_1$–C$_6$)-alkyl)-amino;
- R$^{12}$ is H, (C$_1$–C$_6$)-alkyl which is optionally substituted, once or more than once, by fluorine, (C$_3$–C$_6$)-cylcloalkyl, (C$_3$–C$_6$)-cycloalkyl-C$_1$–C$_4$)-alkyl, (C$_5$–C$_{10}$)-aryl, (C$_5$–C$_{10}$)-aryl-C$_1$–C$_4$)-alkyl, H$_2$N, R$^8$OR$^9$, R$^8$OC(O)R$^9$, R$^8$-(C$_5$–C$_{10}$)-aryl-R$^9$, R$^8$R$^8$NR$^9$, R$^8$NHC(O)R$^9$, R$^8$C(O)NHR$^9$, H$_2$N—C(=NH)—, H$_2$N—C(=NH)—NH— or =O;
  where two adjacent substituents R$^{12}$ can together also be —OCH$_2$O— or —OCH$_2$CH$_2$O—;
- Y is NR$^2$, O or S;
- n is 1 or 2; and
- p and q are, independently of each other, 0 or 1;

in all their stereoisomeric forms and mixtures thereof in all proportions, and their physiologically tolerated salts.

Very particular preference is given to compounds of the formula I in which:

A is one of the radicals

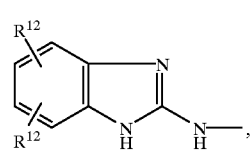

-continued

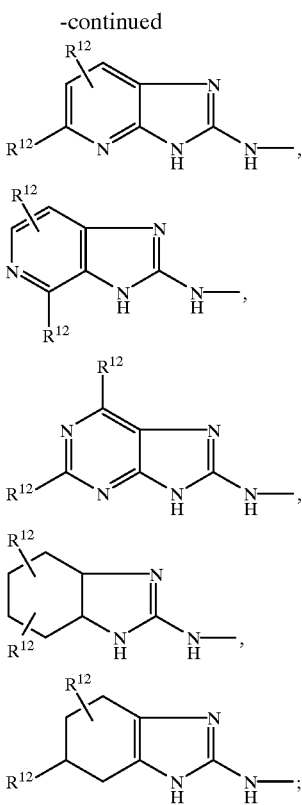

B is a direct linkage, (C₁–C₄)-alkanediyl, phenylene, pyridindiyl, thiophenediyl, furandiyl, cyclohexylene, cyclopentylene, —C≡C— or —CR²=CR³— which can in each case be substituted, once or twice, by (C₁–C₄)-alkyl;

D is a direct linkage, (C₁–C₄)-alkanediyl or phenylene, —O—, —NR²—, —NR²—C(O)—, —C(O)—NR²—, —NR²—S(O)₂, —NR²—C(O)—NR²— or —CR²=CR³— which can in each case be substituted, once or twice, by (C₁–C₄)-alkyl, with it not being possible for D to be —C(O)—NR²— when B is a direct linkage;

E a) is a template from WO 93/08174, U.S. Pat. No. 5,250,679, U.S. Pat. No. 5,403,836 or U.S. Pat. No. 5,565,449, specifically:

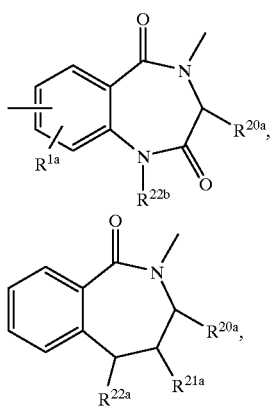

where $R^{1a}$, $R^{20a}$, $R^{21a}$, $R^{22a}$ and $R^{22b}$ are in this case:

$R^{1a}$ is, independently of each other, from one to three groups from the series consisting of hydrogen and halogen (fluorine, chlorine, bromine or iodine);

$R^{20a}$ is hydrogen;

$R^{21a}$ and $R^{22a}$ are, independently of each other,
1. hydrogen,
2. (C₁–C₆)-alkyl,
3. (C₆G₁₂)-aryl,
4. (C₆–C₁₂)-cycloalkyl,
5. (C₁–C₆)-akyl-C₆–C₁₂)-aryl,
6. (C₁–C₆)-akyl-C₆–C₁₂)-cyloalkyl, where the radicals defined under 2. to 6. can be substituted by one or more radicals from the group consisting of fluorine, chlorine, hydroxyl, hydroxamate, sulfonamide, (C₁–C₆)-alkyl, (C₆–C₁₂)-aryl, benzyl or (C₆–C₁₂)-cycloalkyl;

$R^{22b}$ is
1. hydrogen,
2. (C₁–C₁₂)-alkyl,
3. (C₆–C₁₄)-aryl,
4. (C₃–C₁₄)-cycloalkyl,
5. (C₁–C₁₂)-alkyl-(C₆–C₁₄)-aryl,
6. (C₁–C₁₂)-alkyl-(C₃–C₁₄)-cycloalkyl, where the radicals defined under 2. to 6. can be substituted by one or more radicals from the group consisting of halogen (fluorine, chlorine, bromine or iodine); nitro; hydroxyl; carboxyl; tetrazole; hydroxamate; sulfonamide; trifluoroimide; phosphonate; C₁–C₆-alkyl; C₆–C₁₄-aryl; benzyl; C₃–C₁₄cycloalkyl; $COR^{24a}$ or $CONR^{25}R^{26}$; where $R^{24a}$ is a radical from the group consisting of C₁–C₈-alkoxy; C₃–C₁₂-alkenoxy; C₆–C₁₂-aryloxy; di-C₁–C₈-alkylamino-C₁–C₈-alkoxy; acylamino-C₁–C₈-alkoxy, such as acetylaminoethoxy, nicotinoylaminoethoxy, succinamidoethoxy or pivaloylethoxy; or C₆–C₁₂-aryl-C₁–C₈-alkoxy, where the aryl group can be optionally substituted by from one to three radicals selected from the group consisting of nitro, halogen, C₁–C₄-alkoxy, amino, hydroxyl, hydroxy-C₂–C₈-alkoxy or dihydroxy-C₃–C₈-alkoxy;

$R^{25}$ and $R^{26}$ are, independently of each other, hydrogen, C₁–C₁₀-alkyl, C₃–C₁₀-alkenyl, C₆–C₁₄-aryl or C₁–C₆-alkyl-C₆–C₁₀-aryl, or $R^{25}$ and $R^{26}$ together form a trimethylene, tetramethylene, pentamethylene or 3-oxopentamethylene radical;

7. $Q^2$—$L^3$, where
$Q^2$ is hydrogen or $Q^1$; and
$L^3$ is a chemical bond or $L^1$;
$Q^1$ is an amino, amidino, aminoalkylenimino, aminoalkylenamino or guanidino group, preferably an amidino group;
$L^1$ is C₆–C₁₄-aryl-C₂–C₄-alkynylene; C₆–C₁₄-aryl-C₁–C₃-alkylene; C₆–C₁₄-aryl-C₁–C₃-alkyloxyene or —$R^{14c}$—CO—$NR^{6c}R^{15c}$, where $R^{6c}$ is hydrogen, C₁–C₄-alkoxy, C₁–C₄-alkyl or halogen-C₁–C₄-alkyl;

$R^{14c}$ is a chemical bond, C₁–C₈-alkylene, C₃–C₇-cycloalkylene, C₂C₅-alkenylene, C₃–C₅-alkynylene, C₆–C₁₀-arylene, C₁3-alkyl-C₆–C₁₂-arylene, C₁–C₂-alkyl-C₆–C₁₀-aryl-C₁–C₂-alkylene, C₆–C₁₀-aryl-C₁–C₂-alkylene or C₆–C₁₀-aryloxy-C₁–C₂-alkylene, and $R^{15c}$ is a chemical bond, C₁–C₄-alkylen, C₂–C₄-alkenylen, C₂–C₄-alkynylen, C₆–C₁₀-arylen or C₁–C₃-alkyl-C₆4₁₂-arylen;

or b) is a template from WO 95/04057, specifically:

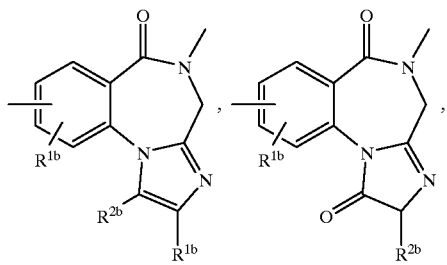
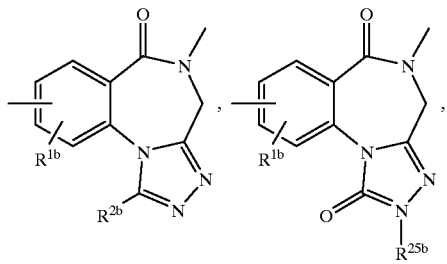
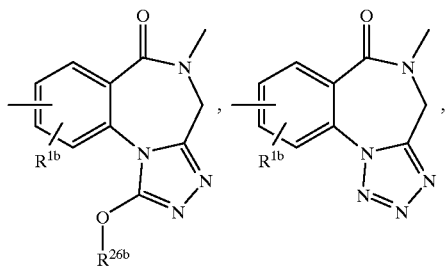

where $R^{1b}$, $R^{2b}$, $R^{25b}$ and $R^{26b}$ are in this case:

- $R^{1b}$ and $R^{2b}$ are, independently of each other, from one to three groups from the series consisting of hydrogen and halogen (fluorine, chlorine, bromine or iodine); and
- $R^{25b}$ and $R^{26b}$ are, independently of each other, hydrogen, $C_1$–$C_{10}$-alkyl, $C_3$–$C_{10}$-alkenyl, $C_6$–$C_{14}$-aryl or $C_1$–$C_6$-alkyl-$C_6$–$C_{10}$-aryl, or $R^{25b}$ and $R^{26b}$ together form a trimethylene, tetramethylene, pentamethylene or 3-oxopentamethylene radical;

or c) is a template from EP 0 655 439, specifically:

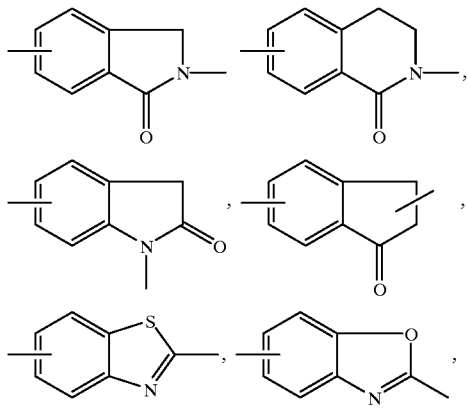

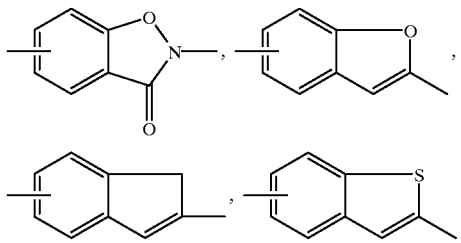

or d) is a template from WO 94/12478, specifically:

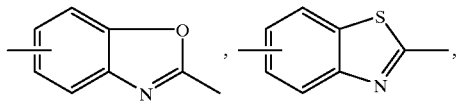

or e) is a template from WO 94/18981, specifically:

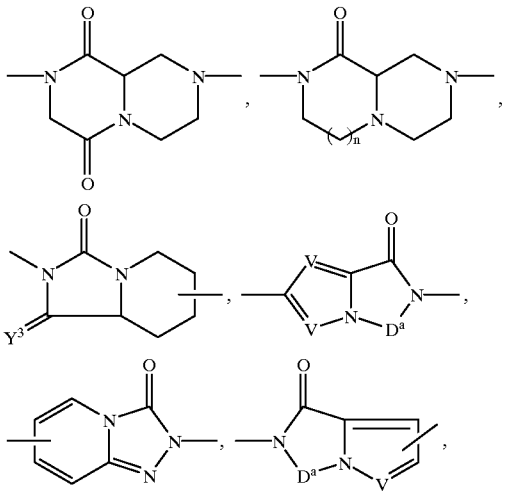

where $Y^3$, V and $D^a$ are defined as described above;
or f) is a template from EP 0 531 883, specifically:

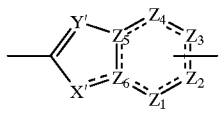

where:
  X' is an oxygen, sulfur or nitrogen atom or an —$NR^{2b}$-group, where
    $R^{2b}$ is a hydrogen atom, a straight-chain or branched alkyl group having from1 to 15 carbon atoms, a straight-chain or branched alkenyl or alkynyl group having in each case from 3 to 10 carbon atoms, where the double bond or triple bond cannot connect directly to the nitrogen atom, a cycloalkyl or cycloalkylalkyl group having in each case from 3 to 7 carbon atoms in the cycloalkyl moiety, an aryl group, an alkyl group having from 2 to 6 carbon atoms which is substituted, from the β position to the nitrogen atom of the —$NR^{2b}$-group onward, by an $R^{3b}O$—, $(R^{3b})_2N$—, $R^{4b}CO$—$NR^{3b}$—, alkylsulfonyl—$NR^{3b}$—, aryisulfonyl-$NR^{3b}$—, alkylsulfenyl, alkylsulfinyl, alkylsulfonyl or $R^{5b}$ group, or an alkyl group having from 1 to 6 carbon atoms which is substituted by one or two aryl groups, $R^{6b}OCO-$, $(R^{3b})_2NCO-$, $R^{5b}-CO-$, $R^{3b}O-CO$-alkylene-$NR^{3b}-CO-$, $(R^{3b})_2N-CO$-alkylene-$NR^{3b}CO-$ or $R^{5b}CO$-alkylene-$NR^{3b}-CO$-group, in which $R^{3b}$ and $R^{5b}$ are defined as indicated below and $R^{6b}$ is a hydrogen atom, an alkyl group having from 1 to 6 carbon atoms, a cycloalkyl group having from 5 to 7 carbon atoms or an aralkyl group, Y is an NO-group, a nitrogen atom or a methine group which is optionally substituted by an alkyl group, $Z_1$, $Z_2$, $Z_3$ and $Z_4$, which can be identical or different, are methine groups, carbon atoms, imino groups or nitrogen atoms, where at least one of the radicals $Z_1$ to $Z_4$ has to contain a carbon atom, and one or two methine groups which are adjacent to a nitrogen atom can in each case be replaced by carbonyl groups, $Z_5$ and $Z_6$ are in each case a carbon atom, or else one of the radicals $Z_5$ or $Z_6$ is a nitrogen atom and the other of the radicals $Z_5$ or $Z_6$ is a carbon atom, $R^{3b}$ is a hydrogen atom, an alkyl group having from 1 to 6 carbon atoms, or an aryl, aralkyl, carboxyalkyl or alkoxycarbonylalkyl group, $R^{4b}$ is a hydrogen atom, an alkyl or alkoxy group having in each case from 1 to 6 carbon atoms, or an aryl or aralkyl group having from 1 to 6 carbon atoms in the alkyl moiety, and $R^{5b}$ is an azetidino, pyrrolidino, hexamethylenimino or heptamethylenimino group or a piperidino group in which the methylene group in the 4 position can be replaced by an oxygen atom, by a sulfenyl, sulfinyl or sulfonyl group, or by an imino group which is substituted by an $R^{3b}$, $R^{4b}CO-$, alkylsulfonyl or arylsulfonyl group, where $R^{3b}$ and $R^{4b}$ are defined as mentioned above, F is a direct linkage, $(C_1-C_6)$-alkanediyl, $-O-$, $-CO-NR^2-$, $-NR^2-CO-$, $-NR^2-C(O)-NR^2-$, $-S(O)_2-NR^2$, $-NR^2-S(O)_2-$, $-CR^2=CR^3-$, or $-C\equiv C-$ which can in each case be substituted, once or twice, by $(C_1-C_4)$-alkyl;

G is

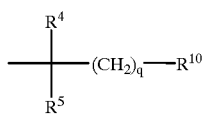

$R^2$ and $R^3$ are, independently of each other, H, $(C_1-C_4)$-alkyl, trifluoromethyl, pentafluoroethyl, $(C_5-C_6)$-cycloalkyl, $(C_5-C_6)$-cycloalkyl-$(C_1-C_4)$-alkyl, phenyl or benzyl;

$R^4$ is $(C_{10}-C_{14})$-cycloalkyl, $(C_{10}-C_{14})$-cycloalkyl-$C_1-C_4)$-alkyl, or $R^{16}OR^9$, $R^{16}NHR^9$, $R^{16}NHC(O)OR^9$, $R^{16}S(O)_nNHR^9$, $R^{16}OC(O)NHR^9$, $R^{16}C(O)NHR^9$, $R^{16}C(O)R^9$, $R^{16}NHC(O)R^9$ or $R^{16}NHS(O)_nR^9$;

$R^5$ is H, $(C_1-C_6)$-alkyl, $(C_5-C_6)$-cycloalkyl, $(C_5-C_6)$-cycloalkyl-$(C_1-C_4)$-alkyl, trifluoromethyl, pentafluoroethyl, phenyl or benzyl;

$R^8$ is H, $(C_1-C_4)$-alkyl, $(C_5-C_6)$-cycloalkyl, $(C_5-C_6)$-cycloalkyl-$(C_1-C_2)$-alkyl, phenyl, benzyl, trifluoromethyl or pentafluoroethyl;

$R^9$ is a direct linkage or $(C_1-C_4)$-alkanediyl;

$R^{10}$ is $C(O)R^{11}$;

$R^{11}$ is OH, $(C_1-C_6)$-alkoxy, phenoxy, benzyloxy, $(C_1-C_4)$-alkylcarbonyloxy-$(C_1-C_4)$-alkoxy, $NH_2$ or mono- or di-$((C_1-C_6)$-alkyl)amino;

$R^{12}$ is H, $(C_1-C_4)$-alkyl, trifluoromethyl, pentafluoroethyl, $(C_5-C_6)$-cycloalkyl, $(C_5-C_6)$-cycloalkyl-$(C_1-C_2)$-alkyl, $(C_5-C_6)$-aryl, $(C_5-C_6)$-aryl-$(C_1-C_2)$-alkyl, $H_2N$, $R^8R^8NR^9$, $R^8NHC(O)R^9$, $H_2N-C(=NH)$ or $H_2N-C(=NH)-NH-$;
where two adjacent substituents $R^{12}$ can also be $-OCH_2O-$ or $-OCH_2CH_2O-$;

$R^{16}$ is $(C_{10}-C_{14})$-cycloalkyl or $(C_{10}-C_{14})$-cycloalkyl-$(C_1-C_4)$-alkyl which can optionally be substituted, once or twice, by $(C_1-C_4)$-alkyl, trifluoromethyl, phenyl, benzyl, $(C_1-C_4)$-alkoxy, phenoxy, benzyloxy, $=O$ or mono- or di-$((C_1-C_4)$-alkyl)-amino, where the cycloalkylene radicals are preferably 1-adamantyl or 2-adamantyl, which can be substituted as described above;

n is 1 or 2; and q is 0 or 1;
in all their stereoisomeric forms and mixtures thereof in all proportions, and their physiologically tolerated salts.

Preference is also given to compounds of the formula I, in which A, B, D, F and G are defined as above for the very particularly preferred compounds of the formula I and E is a template from WO 95/04057, EP 0655 439, WO 94/18981, WO 94/08962, EP 0668 278, WO 94/12478 or EP 0531 883, with the latter preferably being defined as above for the particularly preferred compounds of the formula I, and particularly preferably being defined as above for the very particularly preferred compounds of the formula I.

Another part of the subject-matter of the present invention is that a fibrinogen receptor antagonist, which is known per se, can be converted into a selective vitronectin receptor antagonist by replacing the basic group (with spacer) of a fibrinogen receptor antagonist with the residue A—B—D, which is defined as in Formula I, with the distance between $R^{10}$ and the first N atom in A being from 12 to 13 covalent bonds along the shortest route between these atoms.

In general, compounds of the formula I can be prepared, for example during the course of a convergent synthesis, by linking two or more fragments which can be derived retrosynthetically from the formula I. When preparing the compounds of the formula I, it can, in a general manner, be necessary, during the course of the synthesis, to use a protecting group strategy which is suited to the synthesis problem to temporarily block functional groups which could lead to undesirable reactions or side reactions in the particular synthesis step, as is known to the skilled person. The method of fragment linking is not restricted to the following examples but is generally applicable to syntheses of the compounds of the formula I.

For example, compounds of the formula I of the type

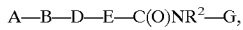

in which $F=C(O)NR^2$, can be prepared by condensing a compound of the formula II

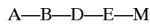    II, where M is hydroxycarbonyl, $(C_1-C_6)$-alkoxycarbonyl or activated carboxylic derivatives, such as acid chlorides, active esters or mixed anhydrides, with $HNR^2-G$.

In order to condense two fragments with the formation of an amide bond, use is advantageously made of the coupling methods, which are known per se, of peptide chemistry (see, for example, Houben-Weyl, Methoden der Organischen Chemie [Methods of Organic Chemistry], Volumes 15/1 and 15/2, Georg Thieme Verlag, Stuttgart, 1974). For this, it is, as a rule, necessary for non-reacting amino groups which are present to be protected with reversible protecting groups during the condensation. The same applies to carboxyl groups which are not involved in the reaction, which carboxyl groups are preferably employed as $(C_1-C_6)$-alkyl, benzyl or tert-butyl esters. There is no necessity to protect amino groups if the amino groups to be generated are still present as nitro or cyano groups and are only formed by means of hydrogenation after the coupling has taken place. After the coupling has taken place, the protecting groups which are present are eliminated in a suitable manner. For example, $NO_2$ groups (guanidino protection), benzyloxycarbonyl groups and benzyl esters can be removed by hydrogenation. The protecting groups of the tert-butyl type are eliminated under acid conditions, while the 9-flubrenylmethyloxycarbonyl radical is removed using secondary amines.

Compounds of the formula I in which $R^{10}=SO_2R^{11}$ are prepared, for example, by oxidizing compounds of the formula I in which $R^{10}=SH$ using methods which are known from the literature (cf. Houben-Weyl, Methoden der Organischen Chemie, Vol. E12/2, Georg Thieme Verlag, Stuttgart 1985, pp. 1058 ff) to give compounds of the formula I in which $R^{10}=SO_3H$, from which the compounds of the formula I in which $R^{10}=SO_2R^{11}$ ($R^{11}\neq OH$) are then prepared directly or by way of corresponding sulfonyl halides by means of esterification or formation of an amide bond. Oxidation-sensitive groups in the molecule, such as amino, amidino or guanidino groups, are, if necessary, protected with suitable protecting groups before performing the oxidation.

Compounds of the formula I in which $R^{10}=S(O)R^{11}$ are prepared, for example, by converting compounds of the formula I in which $R^{10}=SH$ into the corresponding sulfide ($R^{10}=S^\circ$) and then oxidizing with meta-chloroperbenzoic acid to give the sulfinic acids ($R^{10}=SO_2H$) (cf. Houben-Weyl, Methoden der Organischen Chemie, Vol. E11/1, Georg Thieme Verlag, Stuttgart 1985, pp. 618 f), from which the corresponding sulfinic acid esters or amides, $R^{10}=S(O)R^{11}$ ($R^{11}\neq OH$), can be prepared using methods which are known from the literature. In a general manner, other methods known from the literature can also be used to prepare compounds of the formula I in which $R^{10}=S(O)_nR^{11}$ (n=1 or 2) (cf. Houben-Weyl, Methoden der Organischen Chemie, Vol. E11/1, Georg Thieme Verlag, Stuttgart 1985, pp. 618 ff or Vol. E11/2, Stuttgart 1985, pp. 1055 ff).

Compounds of the formula I in which $R^{10}=P(O)(R^{11})n$ (n=1 or 2) are synthesized, using methods which are known from the literature (cf. Houben-Weyl, Methoden der Organischen Chemie, Vols. E1 and E2, Georg Thieme Verlag, Stuttgart 1982), from suitable precursors, with it being necessary to match the selected synthesis method to the target molecule.

Compounds of the formula I in which $R^{10}=C(S)R^{11}$ can be prepared using methods known from the literature (cf. Houben-Weyl, Methoden der Organischen Chemie, Vols. E5/1 and E5/2, Georg Thieme Verlag, Stuttgart 1985).

Compounds of the formula I in which $R^{10}=S(O)_nR^{11}$ (n=1 or 2), $P(O)(R^{11})_n$ (n=1 or 2) or $C(S)R^{11}$ may, of course, also be prepared by means of fragment linking, as described above, which approach is, for example, advisable when, for example, a (commercially available) aminosulfonic acid, aminosulfinic acid, aminophosphonic acid or aminophosphinic acid, or derivatives derived therefrom, such as esters or amides, are present in F—G of the formula I.

Compounds of the formula I in which A—B— is a radical of the formula

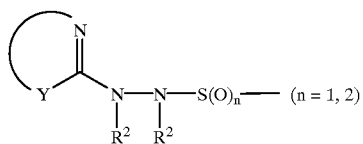

are prepared, using methods which are known from the literature, by reacting compounds of the formula

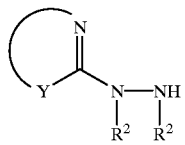

with sulfinic or sulfonic acid derivatives of the formula IV,

    IV in which Q is, e.g., Cl or $NH_2$, in analogy with S. Birtwell et al., J. Chem. Soc. (1946) 491 or Houben Weyl, Methoden der Organischen Chemie, Vol. E4, Georg Thieme Verlag, Stuttgart 1983; p. 620 ff.

Compounds of the formula I in which B is —$NR^2$—C(O)—$NR^2$—, —$NR^2$—C(O)O— or —$NR^2$—C(O)S— and A has the given meaning are prepared, for example, by reacting a compound of the formula V

    V in which Q is $HNR^2$—, HO— or HS—, with a suitable carbonic acid derivative, preferably phosgene, diphosgene (trichloromethyl chloroformate), triphosgene (bis(trichloromethyl) carbonate), ethyl chloroformate, i-butyl chloroformate, bis(1-hydroxy-1-H-benzotriazolyl) carbonate or N,N'-carbonyidiimidazole in a solvent which is inert towards the reagents employed, preferably dimethylformamide (DMF), tetrahydrofuran (THF) or toluene, at a temperature of between −20° C. and the boiling point of the solvent, preferably between 0° C. and 60° C., initially to form a substituted carbonic acid derivative of the formula VI,

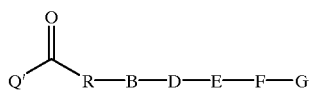    VI in which R is —$NR^2$—, —O— or —S— and Q' is chlorine, methoxy, ethoxy, isobutoxy, benzotriazol-1-oxy or 1-imidazolyl, depending on the carbonic acid derivative employed.

The reaction of these derivatives with the monocycle or polycycle-containing systems of the type VII

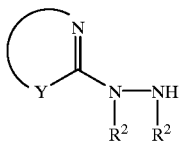
VII is effected in a protic or aprotic, polar but inert organic solvent. In this context, methanol, isopropanol or THF, at temperatures of from 20° C. up to the boiling temperature of these solvents, have proved to be of value when reacting the methyl esters (Q=OMe) with the respective compounds of the formula VII. Most reactions of compounds of the formula VI with salt-free compounds of the formula VII are advantageously carried out in aprotic, inert solvents such as THF, dimethoxyethane or dioxane. However, when a base (such as NaOH) is employed, water can also be used as a solvent when compounds of the formula IV are reacted with the compounds VII. When Q=Cl, the reaction is advantageously carried out with the addition of a base as an acid-wpturing agent, in order to bind the hydrohalic acid.

Compounds of the formula I in which F is $-R^2N-C(O)-NR^2-$ or $-R^2N-C(S)-NR^2-$, are prepared, for example, by reacting a compound of the formula VIII

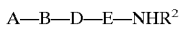
A—B—D—E—NHR$^2$   VIII with an isocyanate OCN—G or isothiocyanate SCN—G using methods which are known from the literature.

Compounds of the formula I in which F is $-C(O)NR^2-$, $-SO_2NR^2-$ or $-(O)O-$ can be obtained, for example, by reacting A—B—D—E—C(O)Q or A—B—D—E—SO$_2$Q (Q is a leaving group which can readily be substituted nucleophilically, for example OH, Cl, OMe, etc.) with HR$^2$N—G or HO—G, respectively, using methods known from the literature.

Compounds of the formula I, in which A is a monocycle or polycycle of the type

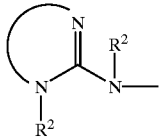

can be prepared, for example, by
a) reacting a compound of the formula IX

HR$^2$N—D—E—F—G   IX with a monocycle or polycycle of the type

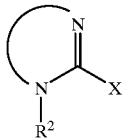

in which X is a leaving group which can be substituted nucleophilically, for example halogen or SH, —SCH$_3$, SOCH$_3$, SO$_2$CH$_3$ or HN—NO2, using methods which are known from the literature (see, e.g., A. F. Mckay et al., J. Med. Chem. 6 (1963) 587, M. N. Buchman et al., J. Am. Chem. Soc. 71 (1949), 766, F. Jung et al., J. Med. Chem. 34 (1991) 1110 or G. Sorba et al., Eur. J. Med. Chem. 21 (1986), 391), or b) reacting a 1,2-diamino compound of the formula XVII

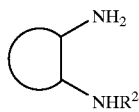
XVII with an isothiocyanate of the formula XIII

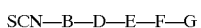
SCN—B—D—E—F—G   XIII to give a thiourea derivative of the formula XVIII

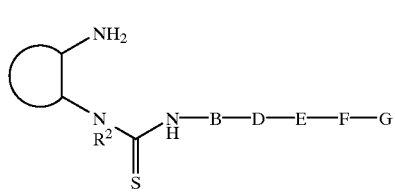
XVIII e.g. in accordance with F. Janssens et al., J. Med. Chem. 28 (1985) 1925, which is then converted, as described in that paper or, for example, in accordance with A.

Mohsen et al., Synthesis (1977) 864 or V. Ojka et al., Indian J. Chem. Sec. B 32 (3) (1993) 394, into the compounds of the formula I in which

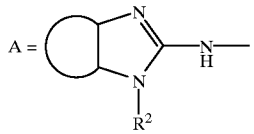

or c) reacting a 1-nitro-2-amino compound of the formula XIX

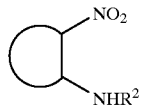
XIX with an isothiocyanate of the formula XIII to give a thiourea derivative of the formula

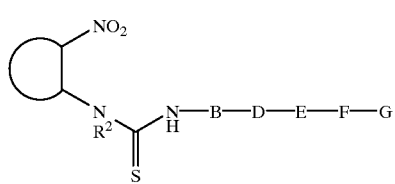
XX which, after reduction of the nitrogroup with Pd/C (cf., e.g., F. Janssens et al., J. Med. Chem. 28 (1985) 1925) as described above, is converted into compounds of the formula I in which A = 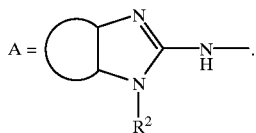

Compounds of the formula I in which A is a monocycle or polycycle of the type

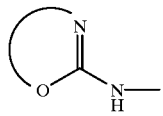

are obtained using methods which are known from the literature, e.g. from compounds of the formula

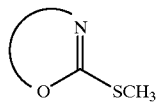

by reaction with compounds of the formula $R^2$—NH—B—D—E—F—G following M. Yamato et al., Chem. Pharm. Bull 32(8) (1984) 3053, or, e.g., from 1,2-aminoalcohols of the formula XII

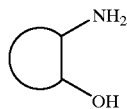 XII which are initially converted, by reaction with isothiocyanates of the formula XIII

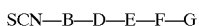 XIII into thioureas of the formula XIV

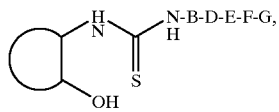 XIV which are then converted, e.g. as described by H. S. Chang et al., Chem. Lett. 8 (1986) 1291 or E. A. Ibrahim et al., J. Heterocycl. Chem. 19(4) (1982) 761, into the compounds of the formula I in which A = 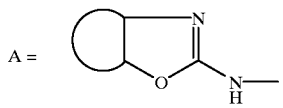

Compounds of the formula I in which A is a monocycle or polycycle of the type

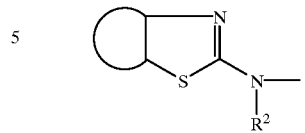

are obtained using methods which are known from the literature, e.g. from 1,2-aminothiols of the formula XV

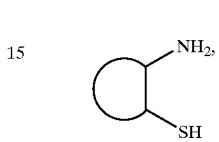 XV which are initially converted, by reaction with isothiocyanates of the formula XIII, into the thioureas of the formula XVI

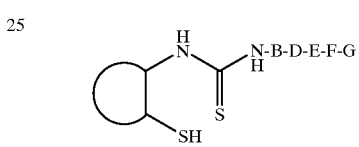 XVI which are then converted, e.g. as described by J. Garvin et al., J. Heterocycl. Chem. 28 (1991) 359 into the compounds of the formula I in which A = 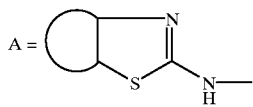

Compounds of the formula I in which D is —C≡C— can be prepared, for example, by reacting a compound of the formula X

 X in which X is I or Br, with a compound of the type A—B—C≡CH in a palladium-catalyzed reaction, as described, for example, in A. Arcadi et al., Tetrahedron Lett. 1993, 34, 2813 or E. C. Taylor et al., J. Org. Chem. 1990, 55, 3222.

In an analogous manner, compounds of the formula I in which F is —C≡C— can be prepared, for example, by linking compounds of the formula XI

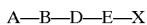 XI in which X is I or Br, with a compound of the type HC≡C—G in a palladium-catalyzed reaction.

The fibrinogen receptor antagonist template E is synthesized as described in the relevant patents, patent applications or publications, with functional groups being incorporated into the template, or being attached to the template, during synthesis of the template or afterwards, preferably during synthesis of the template, which groups permit the subsequent linking-on of A—B—D and F—G by means of fragment linking, as described below, by way of example, for a template from WO 94/18981:

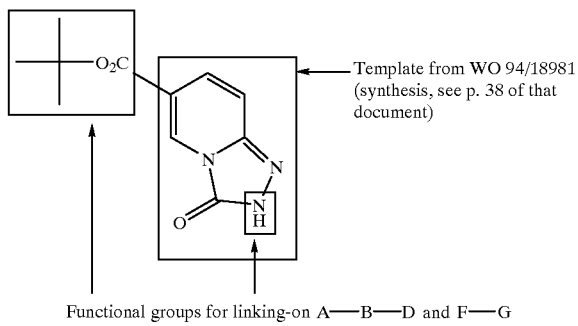

Functional groups for linking-on A—B—D and F—G

Example of the linking-on of A—B—D and F—G

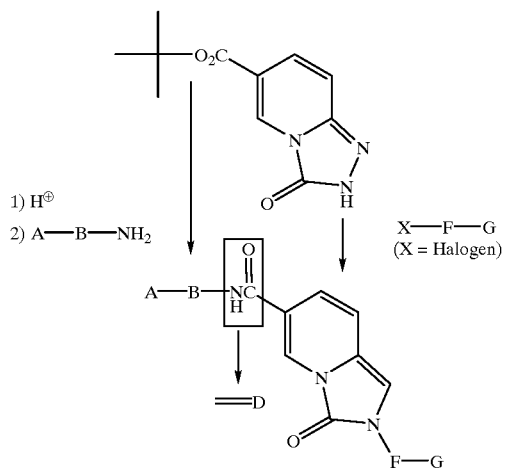

Preparation methods which are known from the literature are described, for example, in J. March, Advanced Organic Chemistry, Third Edition (John Wiley & Sons, 1985).

The compounds of the formula I, and their physiologically tolerated salts, may be administered to animals, preferably to mammals and, in particular, to humans, as drugs on their own, in mixtures with each other or in the form of pharmaceutical preparations which permit enteral or parenteral use and which comprise, as the active constituent, an effective dose of at least one compound of the formula I, or of a salt thereof, together with customary, pharmaceutically unobjectionable carrier and auxiliary substances. The preparations normally comprise from about 0.5 to 90% by weight of the therapeutically active compound.

The drugs may be administered orally, for example in the form of pills, tablets, lacquered tablets, coated tablets, granules, hard and soft gelatin capsules, solutions, syrups, emulsions, suspensions or aerosol mixtures. However, the administration can also be effected rectally, for example in the form of suppositories, or parenterally, for example in the form of injection or infusion solutions, microcapsules or rods, percutaneously, for example in the form of ointments or tinctures, or nasally, for example in the form of nasal sprays.

The pharmaceutical preparations are produced in a manner known per se, with pharmaceutically inert inorganic or organic carrier substances being used. Lactose, corn starch or derivatives thereof, talc, stearic acid or its salts, etc. can, for example, be used for preparing pills, tablets, coated tablets and hard gelatin capsules. Examples of carrier substances for soft gelatin capsules and suppositories are fats, waxes, semisolid and liquid polyols, natural or hardened oils, etc. Examples of suitable carrier substances for preparing solutions and syrups are water, sucrose, invert sugar, glucose, polyols, etc. Suitable carrier substances for preparing injection solutions are water, alcohols, glycerol, polyols, vegetable oils, etc. Suitable carrier substances for microcapsules, implants or rods are mixed polymers of glycolic acid and lactic acid.

In addition to the active compounds and carrier substances, the pharmaceutical preparations may also comprise additives, such as fillers, extenders, disintegrants, binders, glidants, wetting agents, stabilizers, emulsifiers, preservatives, sweeteners, dyes, flavorants or aromatizing substances, thickeners, diluents or buffering substances, and also solvents or solubilizing agents or agents for achieving a slow release effect, and also salts for altering the osmotic pressure, coating agents or antioxidants. They may also comprise two or more compounds of the formula I or their physiologically tolerated salts; they may furthermore comprise one or more different therapeutically active compounds in addition to at least one compound of the formula I.

The dose may be varied within wide limits and must be adjusted to the individual circumstances in each individual case.

In the case of oral administration, the daily dose may be from 0.01 to 100 mg/kg, preferably from 0.1 to 5 mg/kg, particularly from 0.3 to 0.5 mg/kg of bodyweight in order to achieve effective results. In the case of intravenous administration the daily dose also is generally from about 0.01 to 100 mg/kg, preferably from 0.05 to 10 mg/kg of bodyweight. Particularly when administering relatively large quantities, the daily dose can be subdivided into several, e.g. 2, 3 or 4, parts which are administered separately. Where appropriate, it can be necessary to depart from the given daily dose in an upward or downward direction depending on the individual response.

Besides as active drug substances the compounds of the formula I may be used in diagnostic procedures, for example in in vitro diagnoses, or as tools in biochemical research when it is intended to inhibit the vitronectin receptor.

The inhibition of bone resorption by the novel compounds can be determined, for example, using an osteoclast resorption test (PIT ASSAY), for example in analogy with WO 95132710. The test methods which can be used to determine the antagonistic effect of the novel compounds on the vitronectin receptor $\alpha_v\beta_3$ are described below.

Test Method 1:
 Inhibition of the binding of human vitronectin (Vn) to human vitronectin receptor (VnR) $\alpha_v\beta_3$: ELISA test.
1. Purification of human vitronectin
 Human vitronectin is isolated from human plasma and purified by affinity chromatography using the method of Yatohyo et al., Cell Structure and Function, 1988, 23, 281–292.
2. Purification of human vitronectin receptor ($\alpha_v\beta_3$)
 Human vitronectin receptor is isolated from the human placenta using the method of Pytela et al., Methods Enzymol. 1987, 144, 475. Human vitronectin receptor $\alpha_v\beta_3$ can also be isolated from some cell lines (e.g. from 293 cells, which is a human embryonic kidney cell line) which have been cotransfected with DNA sequences for both the subunits, i.e. $\alpha_v$ and $\beta_3$, of the vitronectin receptor. The subunits are extracted with octyl glycoside and then chromatographed through concanavalin A, heparin—Sepharose and S-300.

3. Monoclonal antibodies
Murine monoclonal antibodies which are specific for the $\beta_3$ subunit of the vitronectin receptor are prepared using the method of Newman et al., Blood, 1985, 227–232, or using a similar method. Horseradish peroxidase-conjugated rabbit Fab 2 anti-mouse Fc (anti-mouse Fc HRP) was obtained from Pel Freeze (Catalog No. 715 305–1).
4. ELISA test
Nunc Maxisorp 96-well microtiter plates are coated at 4° C. overnight with a solution of human vitronectin (0.002 mg/ml, 0.05 ml/well) in PBS (phosphate-buffered sodium chloride solution). The plates are washed twice with PBS/0.05% Tween 20 and blocked by incubating (60 min) with bovine serum albumin (BSA, 0.5%, RIA quality or better) in Tris-HCl (50 mM), NaCl (100 mM), MgCl$_2$ (1 mM), CaCl$_2$ (1 mM), MnCl$_2$ (1 mM), pH 7. Solutions of known inhibitors and of the test substances, in concentrations of from $2\times10^{-12}$ to $2\times10^{-6}$ mol/l, are prepared in assay buffer [BSA (0.5%, RIA quality or better) in Tris-HCl (50 mM), NaCl (100 mM), MgCl$_2$ (1 mM), CaCl$_2$ (1 mM), MnCl$_2$ (1 mM), pH 7]. The blocked plates are emptied and in each case 0.025 ml of this solution, which contains a defined concentration (from $2\times10^{-12}$ to $2\times10^{-6}$) of either a known inhibitor or of a test substance, is added to each well. 0.025 ml of a solution of the vitronectin receptor in the test buffer (0.03 mg/ml) is pipetted into each well of the plate and the plate is incubated on a shaker at room temperature for 60–180 min. In the meantime, a solution (6 ml/plate) of a murine monoclonal antibody which is specific for the $\beta_3$ subunit of the vitronectin receptor is prepared in the assay buffer (0.0015 mg/ml). A second rabbit antibody, which is an anti-mouse Fc HRP antibody conjugate, is added to this solution (0.001 ml of stock solution/6 ml of the murine monoclonal anti-$\beta_3$ antibody solution), and this mixture composed of murine anti-$\beta_3$ antibody and rabbit anti-mouse Fc HRP antibody conjugate is left to incubate during the period of the receptor/inhibitor incubation.
The test plates are washed 4 times with PBS solution containing 0.05% Tween-20, and in each case 0.05 ml/well of the antibody mixture is pipetted into each well of the plate and the plate is incubated for 60–180 min. The plate is washed 4 times with PBS/0.05% Tween-20 and then developed with 0.05 ml/well of a PBS solution which contains 0.67 mg/ml o-phenylenediamine and 0.012% H$_2$O$_2$. As an alternative, o-phenylenediamine can be used in a buffer (pH 5) which contains Na$_3$PO$_4$ (50 mM) and citric acid. The color development is stopped with 1N H$_2$SO4 (0.05 ml/well). The absorption of each well is measured at 492–405 nm and the data are evaluated using standard methods.

Test Method 2:
Inhibition of the binding of kistrin to human vitronectin receptor (VnR) $\alpha_v\beta_3$: ELISA test
1. Purification of kistrin
Kistrin is purified using the methods of Dennis et al., as described in Proc. Natl. Acad. Sci. USA 1989, 87, 2471–2475 and PROTEINS: Structure, Function and Genetics 1993, 15, 312–321.
2. Purification of human vitronectin receptor ($\alpha_v\beta_3$) see test method 1.
3. Monoclonal antibodies
see test method 1.
4. ELISA test
The ability of substances to inhibit the binding of kistrin to the vitronectin receptor can be ascertained using an ELISA test. For this purpose, Nunc 96-well microtiter plates are coated with a solution of kistrin (0.002 mg/ml) using the method of Dennis et al., as described in PROTEINS: Structure, Function and Genetics 1993, 15, 312–321. The subsequent experimental implementation of the ELISA test is as described in test method 1, item 4.

Test Method 3:
Inhibition of the binding of $\alpha_v\beta_3$-transfected 293 cells to human vitronectin:
Cell Test
293 cells, a human embryonic kidney cell line, which are cotransfected with DNA sequences for the $\alpha_v$ and $\beta_3$ subunits of the vitronectin receptor $\alpha_v\beta_3$ are selected for a high rate of expression (>500,000 $\alpha_v\beta_3$ receptors/cell) using the FACS method. The selected cells are cultured and re-sorted by FACS in order to obtain a stable cell line (15 D) having expression rates of >1,000,000 copies of $\alpha_v\beta_3$ per cell.

A Limbro 96-well tissue culture plate having a flat bottom is coated at 4° C. overnight with human vitronectin (0.01 mg/ml, 0.05 ml/well) in phosphate-buffered sodium chloride solution (PBS) and then blocked with 0.5% BSA. Solutions of the test substances having concentrations of from $10^{10}$ to $2\times10^{-3}$ mol/l are prepared in glucose-containing DMEM medium, and in each case 0.05 ml/well of the solution is added to the plate. The cells which are expressing high levels of $\alpha_v\beta_3$ (e.g. 15 D) are suspended in glucose-containing DMEM medium and the suspension is adjusted to a content of 25,000 cells/0.05 ml of medium. 0.05 ml of this cell suspension is then added to each well and the plate is incubated at 37° C. for 90 min. The plate is washed 3× with warm PBS in order to remove unbound cells. The bound cells are lysed in citrate buffer (25 mM, pH 5.0) containing 0.25% Triton X-100. The hexose amidase substrate p-nitrophenyl-N-acetyl-$\beta$-D-glucosaminide is then added and the plate is incubated at 37° C. for 90 min. The reaction is stopped with a glycine (50 mM)/EDTA (5 mM) buffer (pH 10.4) and the absorption of each well is measured at 405–650 nm.

The antagonistic effect of the compounds of the present invention on the fibrinogen receptor $\alpha_{IIb}\beta_3$, in particular for determining selectivity, can be ascertained as described in U.S. Pat. No. 5,403,836, p. 237.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure or all publications cited above are expressly incorporated herein by reference in their entireties to the same extent as if each were incorporated by reference individually. The disclosure of German Patent Application No. 196 53 645.6, is incorporated herein in its entirety.

What is claimed is:
1. A compound of formula 1,

 (1)

in which:
A is

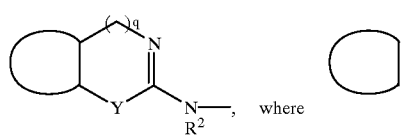, where is a 5-membered to 10-membered monocyclic or polycyclic, aromatic or nonaromatic ring system which can contain from 1 to 4 heteroatoms selected from the group consisting of N, O and S and can optionally be substituted, once or more than once, by $R^{12}$, $R^{13}$, $R^{14}$ and $R^{15}$, B is a direct linkage, $(C_1-C_8)$-alkanediyl,$(C_5-C_{10})$-arylene, $(C_3-C_8)$-cycloalkylene, —C≡C—, —NR$^2$—, —NR$^2$—C(O)—, —NR$^2$—C(O)—NR$^2$—, NR$^2$—C(S)—NR$^2$—, —O—C(O)—, —NR$^2$—S(O)—, —NR$^2$—S(O)$_2$—, —O—, —S— or —CR$^2$=CR$^3$—, which can in each case be substituted, once or twice, by $(C_1-C_8)$-alkyl;

D is a direct linkage, $(C_1-C_8)$-alkanediyl, $(C_5-C_{10})$-arylene —O—, —NR$^2$—, —CO—NR$^2$—, NR$^2$—CO—, —NR$^2$—C(O)—NR$^2$—, —NR$^2$—C(S)—NR$^2$—, —OC(O)—, —C(O)O—, —S(O)—, —S(O)$_2$—, —S(O)$_2$—NR$^2$—, S(O)—NR$^2$—, —NR$^2$—S(O)—, —NR$^2$—S(O)$_2$—, S—, —CR$^2$=CR$^3$— or —C≡C— which can in each case be substituted, once or twice, by $(C_1-C_8)$-alkyl, —CR$^2$=CR$^3$— or $(C_5-C_6)$-aryl, provided that D is not —CO—NR$^2$—, —C(O)O—, —S(O)—, —S(O)$_2$—, —S(O)—NR$^2$— or —S(O)$_2$—NR$^2$— when B is a direct linkage;

E is

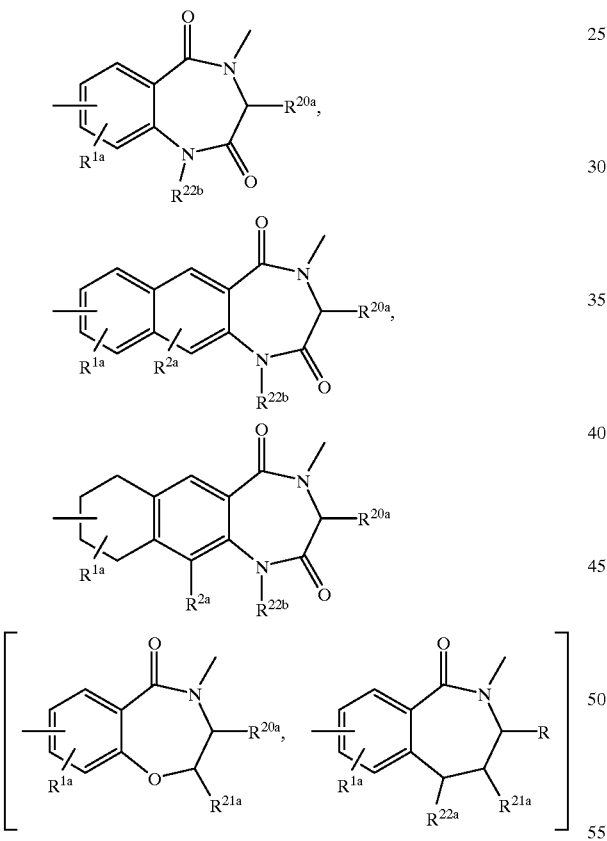

where:
$R^{1a}$ and $R^{2a}$ are, independently of each other, from one to three groups selected from the series consisting of hydrogen, halogen, cyano, carboxamido, carbamoyloxy, formyloxy, formyl, azido, nitro, ureido, thioureido, hydroxyl, mercapto or sulfonamido, and an optionally substituted radical selected from the group consisting of $C_1-C_{12}$-alkyl, $C_2-C_{12}$-alkenyl, $C_3-C_{12}$-alkynyl, $C_3-C_{12}$-cycloalkyl, $C_6-C_{14}$-aryl, $C_6-C_{10}$-aryl-$C_1-C_8$-alkyl, $C_1-C_{12}$-alkyloxy, $C_6-C_{14}$-aryloxy and $C_1-C_{12}$-acylamino, where the substituents are a radical selected from the group consisting of halogen, cyano, azido, nitro, hydroxyl, mercapto, sulfonamido, ureido, thioureido, carboxamido, carbamoyloxy, formyloxy, formyl, $C_1-C_4$-alkoxy, phenyl and phenoxy;

$R^{20a}$ is hydrogen, halogen, $C_1-C_4$-alkoxy, $C_1-C_4$-alkyl, phenyl, benzyl or halogen-$C_1-C_4$-alkyl, and $R^{22b}$ is:
(i) hydrogen
(ii) $(C_1-C_{12})$-alkyl
(iii) $(C_6-C_{14})$-aryl
(iv) $(C_3-C_{14})$-cycloalkyl
(v) $(C_1-C_{12})$-alkyl-$(C_6-C_{14})$-aryl,
(vi) $(C_1-C_{12})$-alkyl-$(C_3-C_{14})$-cycloalkyl, where the radicals defined under (ii) to (vi) can be substituted by one or more radicals selected from the group consisting of halogen; nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; COR$^{24a}$ and CONR$^{25}$R$^{26}$; where $R^{24a}$ is a radical selected from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy; acetylaminoethoxy; nicotinoylaminoethoxy; succinamidoethoxy; pivaloylethoxy; and $C_6-C_{12}$-aryl-$C_1-C_8$-alkoxy, where the aryl group can optionally be substituted by from one to three radicals selected from the group consisting of nitro, halogen, $C_1-C_4$-alkoxy, amino, hydroxyl, hydroxy-$C_2-C_8$-alkoxy and dihydroxy-$C_3-C_8$-alkoxy;

$R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or $R^{25}$ and $R^{26}$ together form a trimethylene, tetramethylene, pentamethylene or 3-oxopentamethylene radical; or (vii) $Q^2$—$L^3$, where
$Q^2$ is hydrogen or $Q^1$; and
$L^3$ is a direct linkage, $L^1$ or $L^2$;
$Q^1$ is a substituted or unsubstituted, positively charged, nitrogen-containing radical;
$L^1$ is a divalent radical which contains from 3 to 9 methylene groups, where from one to all the methylene groups can be replaced with one or more alkene radicals, alkyne radicals, aryl radicals or heteroatoms selected from the group consisting of N, O and S, and amide group, and
$L^2$ is an optionally substituted, divalent radical;

F is defined like D;

G is

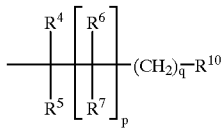

wherein
$R^2$ and $R^3$ are, independently of each other, hydrogen, $(C_1-C_{10})$-alkyl, which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $R^8OC(O)R^9$, $R^8R^8NC(O)R^9$ or $R^8C(O)R^9$;

$R^4$, $R^5$, $R^6$ and $R^7$ are, independently of each other, hydrogen, fluorine, OH, $(C_1-C_8)$-alkyl, $(C_3-C_{14})$- cycloalkyl, $(C_3-C_{14})$-cycloalkyl-$(C_1-C_8)$-alkyl, or $R^8OR^9$, $R^8SR^9$, $R^8CO_2R^9$, $R^8OC(O)R^9$, $R^8-(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is hydrogen, $(C_1-C_8)$-alkyl, $(C_3-C_{14})$-cycloalkyl, $(C_3-C_{14})$-cycloalkyl-$(C_1-C_8)$-alkyl, $(C_5-C_{14})$-aryl or $(C_5-C_{14})$-aryl-$(C_1-C_8)$-alkyl, where the alkyl radicals can be substituted, once or more than once, by fluorine;

$R^9$ is a direct linkage or $(C_1-C_8)$-alkanediyl;

$R^{10}$ is $C(O)R^{11}$, $C(S)R^{11}$, $S(O)_nR^{11}$, $P(O)(R^{11})_2$ or a four-membered to eight-membered, saturated or unsaturated heterocycle which contains 1, 2, 3 or 4 heteroatoms selected from the group consisting of N, O and S;

$R^{11}$ is OH, $(C_1-C_8)$-alkoxy, $(C_5-C_{14})$-aryl-$(C_1-C_8)$-alkoxy, $(C_5-C_{14})$-aryloxy, $(C_1-C_8)$-alkylcarbonyloxy-$(C_1-C_4)$-alkoxy, $(C_5-C_{14})$-aryl-$(C_1-C_8)$-alkylcarbonyloxy-$(C_1-C_6)$-alkoxy, $NH_2$, mono- or di-$((C_1-C_8)$-alkyl)-amino, $(C_5-C_{14})$-aryl-$(C_1-C_8)$-alkylamino, $(C_1-C_8)$-dialkylaminocarbonylmethyloxy, $(C_5-C_{14})$-aryl-$(C_1-C_8)$-dialkylaminocarbonylmethyloxy or $(C_5-C_{14})$-arylamino or the radical of an L-amino acid or D-amino acid;

$R^{12}$, $R^{13}$, $R^{14}$ and $R^{15}$ are, independently of each other, hydrogen, $(C_1-C_{10})$-alkyl which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $H_2N$, $R^8ONR^9$, $R^8OR^9$, $R^8OC(O)R^9$, $R^8R^8NR^9$, $R^8-(C_5-C_{14})$-aryl-$R^9$, HO—$(C_1-C_8)$alkyl-$N(R^2)R^9$, $R^8N(R^2)C(O)R^9$, $R^8C(O)N(R^2)R^9$, $R^8C(O)R^9$, $R^2R^3N-C(=NR^2)-NR^2$, $R^2R^3N-C(=NR^2)$, =O, or =S;

where two adjacent substituents from $R^{12}$ to $R^{15}$ can also together be —OCH$_2$O—, —OCH$_2$CH$_2$O— or —OC(CH$_3$)$_2$O—;

Y is $NR^2$, O or S;

n is 1 or 2;

p and q are, independently of each other, 0 or 1;

in all its stereoisomeric forms and mixtures thereof in all proportions, and its physiologically tolerated salts.

2. A compound of the formula 1 as claimed in claim 1, in which:

A is the radial

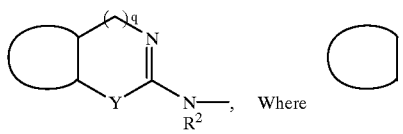

Is a 5-membered to 10-membered monocyclic or polycyclic, aromatic or nonaromatic ring system which can contain from 1 to 4 heteroatoms selected from the group consisting of N, O and S and which can optionally be substituted, once or more than once, by $R^{12}$, $R^{13}$, $R^{14}$ and $R^{15}$.

B is a direct linkage, $(C_1-C_6)$-alkanediyl, $(C_5-C_8)$-arylene, $(C_3-C_8)$-cycloalkylene, —C≡C—, —NR$^2$—, —NR$^2$—C(O)—, —NR$^2$—C(O)—NR$^2$—, —NR$^2$—S(O)—, —NR$^2$—S(O)$_2$—, —O— or —CR$^2$=CR$^3$— which can in each case be substituted, once or twice, by $(C_1-C_6)$-alkyl;

D is a direct linkage, $(C_1-C_8)$-alkanediyl, $(C_5-C_8)$-arylene, —O—, —NR$^2$—, —CO—NR$^2$—, —NR$^2$—CO—, —NR$^2$—C(O)—NR$^2$—, —OC(O)—, —C(O)O—, —S(O)$_2$—, —S(O)$_2$—NR$^2$—, —NR$^2$—S(O)$_2$—, —S—, —CR$^2$=CR$^3$— or —C≡C— which can in each case be substituted, once or twice, by $(C_1-C_8)$-alkyl, —CR$^2$=CR$^3$— or $(C_5-C_6)$-aryl, provided that D is not —CO—NR$^2$—, —C(O)O—, —SO$_2$— or —S(O)$_2$—NR$^2$— when B is a direct linkage;

F is defined like D;

G is

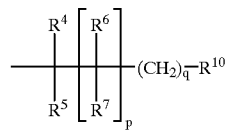

$R^2$ and $R^3$ are, independently of each other, hydrogen, $(C_1-C_{10})$-alkyl, which is optionally substituted, once or more than once, by fluorine, $(C_3-C_8)$-cycloalkyl, $(C_3-C_8)$-cycloalkyl-$(C_1-C_6)$-alkyl, $(C_5-C_{12})$-aryl, $(C_5-C_{12})$-aryl-$(C_1-C_6)$-alkyl, $R^8OC(O)R^9$, $R^8R^8NC(O)R^9$ or $R^8C(O)R^9$;

$R^4$, $R^5$, $R^6$ and $R^7$ are, independently of each other, hydrogen, fluorine, OH, $(C_1-C_8)$-alkyl, $(C_5-C_{14})$-cycloalkyl, $(C_5-C_{14})$-cycloalkyl-$(C_1-C_8)$-alkyl, or $R^8OR^9$, $R^8SR^9$, $R^8CO_2R^9$, $R^8OC(O)R^9$, $R^8-(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is hydrogen, $(C_1-C_8)$-alkyl, $(C_5-C_{14})$-cycloalkyl, $(C_5-C_{14})$-cycloalkyl-$(C_1-C_6)$-alkyl, $(C_5-C_{12})$-aryl or $(C_5-C_{12})$-aryl-$(C_1-C_6)$-alkyl, where the alkyl radicals can be substituted, once or more than once, by fluorine;

$R^9$ is a direct linkage or $(C_1-C_6)$-alkanediyl;

$R^{10}$ is $C(O)R^{11}$, $C(S)R^{11}$, $S(O)_nR^{11}$, $P(O)(R^{11})_2$ or a four-membered to eight-membered, saturated or unsaturated heterocycle which contains 1, 2, 3 or 4 heteroatoms selected from the group consisting of N, O and S;

$R^{11}$ is OH, $(C_1-C_6)$-alkoxy, $(C_5-C_{12})$-aryl-$(C_1-C_6)$-alkoxy, $(C_5-C_{12})$-aryloxy, $(C_1-C_6)$-alkylcarbonyloxy-$(C_1-C_4)$-alkoxy, $(C_5-C_{12})$-aryl-$(C_1-C_6)$-alkylcarbonyloxy-$(C_1-C_6)$-alkoxy, $NH_2$, mono- or di-$((C_1-C_6)$-alkyl)-amino, $(C_5-C_{12})$-aryl-$(C_1-C_6)$-alkylamino, $(C_1-C_6)$-dialkylaminocarbonylmethyloxy;

$R^{12}$, $R^{13}$, $R^{14}$ and $R^{15}$ are, independently of each other, hydrogen, $(C_1-C_8)$-alkyl which is optionally substituted, once or more than once, by fluorine, $(C_3-C_8)$-cycloalkyl, $(C_3-C_8)$-cycloalkyl-$(C_1-C_6)$-alkyl, $(C_5-C_{12})$-aryl, $(C_5-C_{12})$-aryl-$(C_1-C_6)$-alkyl, $H_2N$, $R^8ONR^9$, $R^8OR^9$, $R^8OC(O)R^9$, $R^8R^8NR^9$, $R^8-(C_5-C_{12})$-aryl-$R^9$, $R^8R^8NR^9$, HO—$(C_1-C_8)$-alkyl-$N(R^2)R^9$, $R^8N(R^2)C(O)R^9$, $R^8C(O)N(R^2)R^9$, $R^8C(O)R^9$, $R^2R^3N-C(=NR^2)$, $R^2R^3N-C(=NR^2)-NR^2$, =O, or =S;

where two adjacent substituents from $R^{12}$ to $R^{15}$ can also together be —OCH$_2$O——OCH$_2$CH$_2$O— or —OC(CH$_3$)$_2$O—;

Y is $NR^2$, O or S;

p and q are, independently of each other, 0 or 1;

and E is as defined in claim 1;

in all its stereoisomeric forms and mixtures thereof in all proportions, and its physiologically tolerated salts.

3. A compound of the formula 1 as claimed in claim 1, in which:

A is one of the radicals

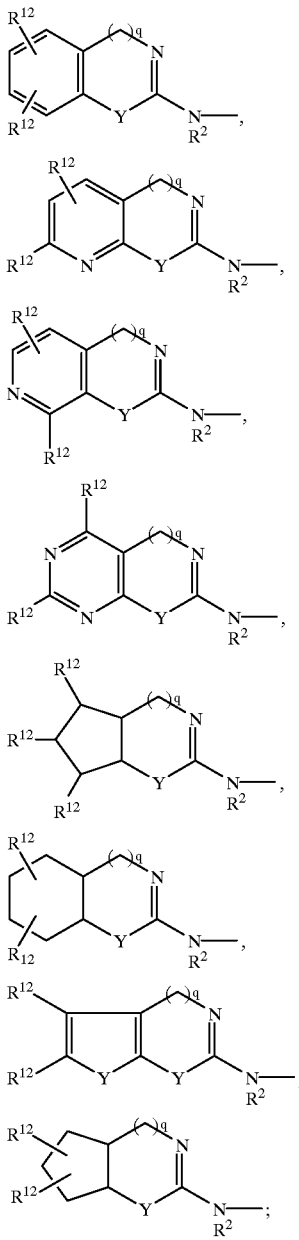

B is a direct linkage, $(C_1-C_6)$-alkanediyl, $(C_5-C_6)$-arylene, $(C_5-C_6)$-cycloalkylene, —C≡C—, —NR$^2$—, —NR$^2$—C(O)—, —NR$^2$—S(O)$_2$—, —O— or —CR$^2$=CR$^3$—, which can in each case be substituted, once or twice, by $(C_1-C_6)$-alkyl;

D is a direct linkage, $(C_1-C_6)$-alkanediyl, $(C_5-C_6)$-arylene, —O—, —NR$^2$—, —NR$^2$—C(O)—, —C(O) NR$^2$—, —NR$^2$—C(O)—NR$^2$—, —OC(O)—, —S(O)$_2$—NR$^2$—, —NR$^2$—S(O)$_2$— or —CR$^2$=C$^3$— which can in each case be substituted, once or twice, by $(C_1-C_6)$-alkyl, provided that D is not —C(O)NR$^2$— or —S(O)$_2$—NR$^2$— when B is a direct linkage;

E is defined as in claim 1;

F is a direct linkage, $(C_1-C_6)$-alkanediyl, —O—, —CO—NR$^2$—, —NR$^2$—CO—, —NR$^2$—C(O)—NR$^2$—, —OC(O)—, —C(O)O—, —S(O)$_2$—, —S(O)$_2$—NR$^2$—, —NR$^2$—S(O)$_2$—, —CR$^2$=CR$^3$—, or —C≡C— which can in each case be substituted, once or twice, by $(C_1-C_6)$-alkyl; and G is

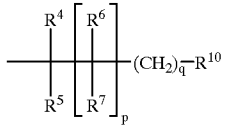

wherein $R_2$ and $R_3$ are, independently of each other, hydrogen, $(C_1-C_6)$-alkyl which is optionally substituted, once or more than once, by fluorine, $(C_5-C_6)$-cycloalkyl, $(C_5-C_6)$-cycloalkyl-$(C_1-C_4)$-alkyl, $(C_5-C_{10})$-aryl, $(C_5-C_{10})$-aryl-$(C_1-C_4)$-alkyl, $R^8OC(O)R^9$, $R^8R^8NC(O)R^9$ or $R^8C(O)R^9$;

$R^4$, $R^5$, $R^6$ and $R^7$ are, independently of each other, hydrogen, fluorine, OH, $(C_{1-C6})$-alkyl, $(C_5-C_{14})$-cycloalkyl, $(C_5-C_{14})$-cycloalkyl-$(C_1-C_6)$-alkyl, or $R^8OR^9$, $R^8CO_2R^9$, $R^8OC(O)R^9$, $R^8$—$(C_5-C_{10})$-aryl-$R^9$, $R^8NHR^9$, $R^8R^8NR^9$, $R^8NHC(O)OR^9$, $R^8S(O)_n$NHR$^9$, $R^8OC(O)NHR^9$, $R^8C(O)NHR^9$, $R^8C(O)R^9$, $R^8NHC(O)NHR^9$, $R^8NHS(O)_nNHR^9$, $R^8NHC(O)R^9$ or $R^8NHS(O)_nR^9$, where are least one of the groups $R^4$, $R^5$, $R^6$ and $R^7$ is a lipophilic radical;

$R^8$ is hydrogen, $(C_1-C_6)$-alkyl, $(C_5-C_{14})$-cycloalkyl, $(C_5-C_{14})$-cycloalkyl-$(C_1-C_4)$-alkyl, $(C_5-C_{10})$-aryl or $(C_5-C_{10})$-aryl-$(C_1-C_4)$-alkyl, where the alkyl radicals can be substituted by from 1 to 6 fluorine atoms;

$R^9$ is a direct linkage or $(C_1-C_6)$-alkanediyl;

$R^{10}$ is $C(O)R^{11}$;

$R^{11}$ is OH, $(C_1-C_6)$-alkoxy, $(C_5-C_{10})$-aryl-$(C_1-C_6)$-alkoxy, $(C_5-C_{10})$-aryloxy, $(C_1-C_6)$-alkylcarbonyloxy-$(C_1-C_4)$-alkoxy, $(C_5-C_{10})$-aryl-$(C_1-C_4)$-alkylcarbonyloxy-$(C_1-C_4)$-alkoxy, NH$_2$ or mono- or di-$((C_1-C_6)$-alkyl)-amino;

$R^{12}$ is hydrogen, $(C_1-C_6)$-alkyl which is optionally substituted, once or more than once, by fluorine, $(C_3-C_6)$-cycloalkyl, $(C_3-C_6)$-cycloalkyl-$(C_1-C_4)$-alkyl, $(C_5-C_{10})$-aryl, $(C_5-C_{10})$-aryl-$(C_1-C_4)$-alkyl, H$_2$N, $R^8OR^9$, $R^8OC(O)R^9$, $R^8$—$(C_5-C_{10})$-aryl-$R^9$, $R^8R^8NR^9$, $R^8NHC(O)R^9$, $R^8C(O)NHR^9$, H$_2$N—C(=NH)—, H$_2$N—C(=NH)—NH— or =O;

where two adjacent substituents $R^{12}$ can together also be —OCH$_2$O— or —OCH$_2$CH$_2$O—;

Y is NR$_2$, O or S;

n is 1 or 2; and p and q are, independently of each other, 0 or 1;

in all its stereoisomeric forms and mixtures thereof in all proportions, and its physiologically tolerated salts.

4. A compound of the formula 1 as claimed in claim 1, in which:

A is one of the radicals

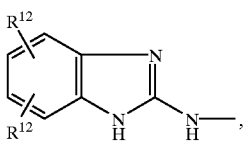

-continued

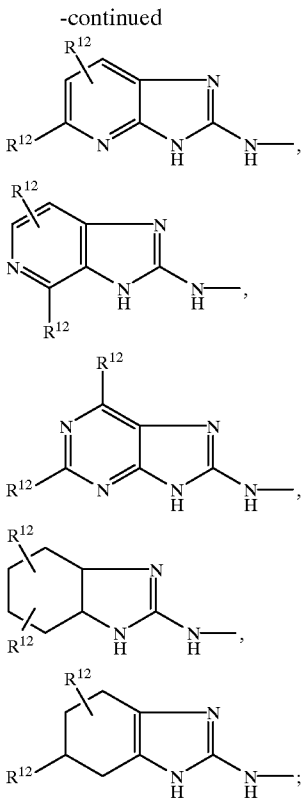

B is a direct linkage, $(C_1-C_4)$-alkanediyl, phenylene, pyridindiyl, thiophenediyl, furandiyl, cyclohexylene, cyclopentylene, —C≡C— or —CR$^2$=CR$^3$— which can in each case be substituted, once or twice, by $(C_1-C_4)$-alkyl;

D is a direct linkage, $(C_1-C_4)$-alkanediyl, phenylene, —O—, —NR$^2$—, —NR$^2$—C(O)—, —C(O)—NR$^2$—, —NR$^2$—S(O)$_2$, —NR$^2$—C(O)—NR$^2$— or —CR$^2$=CR$^3$— which can in each case be substituted, once or twice, by $(C_1-C_4)$-alkyl, provided that D is not —C(O)—NR$^2$— when B is a direct linkage;

E a) is

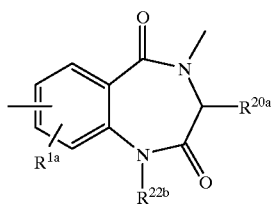

where:
R$^{1a}$ is, independently of each other, selected from one to three groups selected from the series consisting of hydrogen and halogen;
R$^{20a}$ is hydrogen;
R$^{22b}$ is
(i) hydrogen
(ii) $(C_1-C_{12})$-alkyl,
(iii) $(C_6-C_{14})$-aryl,
(iv) $(C_3-C_{14})$-cycloalkyl,
(v) $(C_1-C_{12})$-alkyl-$(C_6-C_{14})$-aryl,
(vi) $(C_1-C_{12})$-alkyl-$(C_3-C_{14})$-cycloalkyl, where the radicals defined under (ii) to (vi) can be substituted by one or more radicals selected from the group consisting of halogen; nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; COR$^{24a}$ and CONR$^{25}$R$^{26}$; where R$^{24a}$ is a radical selected from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy; acetylaminoethoxy; nicotinoylaminoethoxy; succinamidoethoxy; pivaloylethoxy; and $C_6-C_{12}$-aryl-$C_1-C_8$-alkoxy, where the aryl group can be optionally substituted by from one to three radicals selected from the group consisting of nitro, halogen, $C_1-C_4$-alkoxy, amino, hydroxyl, hydroxy-$C_2-C_8$-alkoxy and dihydroxy-$C_3-C_8$-alkoxy;
R$^{25}$ and R$^{26}$ are, independently of each other, hydrogen $C_1-C_{10}$-alkyl, $C_3-C_{10}$-alkenyl, $C_6-C_{14}$-aryl or $C_1-C_6$-alkyl-$C_6-C_{10}$-aryl, or
R$^{25}$ and R$^{26}$ together form a trimethylene, tetramethylene, pentamethylene or 3-oxopentamethylene radical; or (vii) Q$^2$—L$^3$, where
Q$^2$ is hydrogen or Q$^1$; and
L$^3$ is a direct linkage or L$^1$;
Q$^1$ is an amino, amidino, aminoalkylenimino, iminoalkylenamino or guanidino group;
L$^1$ is $C_6-C_{14}$-aryl-$C_2-C_4$-alkynylene; $C_6-C_{14}$-aryl-$C_1-C_3$-alkylene; $C_6-C_{14}$-aryl-$C_1-C_3$-alkyloxyene or —R$^{14c}$—CO—NR$^{6c}$R$^{15c}$, where
R$^{6c}$ is hydrogen, $C_1-C_4$-alkoxy, $C_1-C_4$-alkyl or halogen-$C_1-C_4$-alkyl;
R$^{14c}$ is a direct linkage, $C_1-C_8$-alkylene, $C_3-C_7$-cycloalkylene, $C_2-C_5$-alkenylene, $C_3-C_5$-alkynylene, $C_6-C_{10}$-arylene, $C_1-C_3$-alkyl-$C_6-C_{12}$-arylene, $C_1-C_2$-alkyl-$C_6-C_{10}$-aryl-$C_1-C_2$-alkylene, $C_6-C_{10}$-aryl-$C_1-C_2$-alkylene or $C_6-C_{10}$-aryloxy-$C_1-C_2$-alkylene, and
R$^{15c}$ is a chemical bond, $C_1-C_4$-alkylene, $C_2-C_4$-alkenylene, $C_2-C_4$-alkynylene, $C_6-C_{10}$-arylene or $C_1-C_3$-alkyl-$C_6-C_{12}$-arylene;

F is a direct linkage, $(C_1-C_6)$-alkanediyl, —O—, —CO—NR$^2$—, —NR$^2$—CO—, —NR$^2$—C(O)—NR$^2$—, —S(O)$_2$—NR$^2$, —NR$^2$—S(O)$_2$—, —CR$^2$=CR$^3$—, or —C≡C— which can in each case be substituted, once or twice, by $(C_1-C_4)$-alkyl;

G is

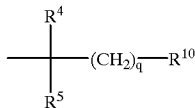

wherein:
R$^2$ and R$^3$ are, independently of each other, hydrogen, —$(C_1-C_4)$-alkyl, trifluoromethyl, pentafluoroethyl, $(C_5-C_6)$-cycloalkyl, $(C_5-C_6)$-cycloalkyl-$(C_1-C_4)$-alkyl, phenyl or benzyl;
R$^4$ is $(C_{10}-C_{14})$-cycloalkyl, $(C_{10}-C_{14})$-cycloalkyl-$(C_1-C_4)$-alkyl, or R$^{16}$OR$^9$, R$^{16}$NHR$^9$, R$^{16}$NHC(O)OR$^9$, R$^{16}$S(O)$_n$—NHR$^9$, R$^{16}$OC(O)NHR$^9$, R$^{16}$C(O)NHR$^9$, R$^{16}$C(O)R$^9$, R$^{16}$NHC(O)R$^9$ or R$^{16}$NHS(O)$_n$R$^9$;
R$^5$ is hydrogen, $(C_1-C_6)$-alkyl, $(C_5-C_6)$-cycloalkyl, $(C_5-C_6)$-cycloalkyl-$(C_1-C_4)$-alkyl, trifluoromethyl, pentafluoroethyl, phenyl or benzyl;
R$^8$ is hydrogen, $(C_1-C_4)$-alkyl, $(C_5-C_6)$-cycloalkyl, $(C_5-C_6)$-cycloalkyl-$(C_1-C_2)$-alkyl, phenyl, benzyl, trifluoromethyl or pentafluoroethyl;

$R^9$ is a direct linkage or $(C_1-C_4)$-alkanediyl;

$R^{10}$ is $C(O)R^{11}$;

$R^{11}$ is OH, $(C_1-C_6)$-alkoxy, phenoxy, benzyloxy, $(C_1-C_4)$-alkylcarbonyloxy-$(C_1-C_4)$-alkoxy, $NH_2$ or mono- or di-$((C_1-C_6)$-alkyl)amino;

$R^{12}$ is hydrogen, $(C_1-C_4)$-alkyl, trifluoromethyl, pentafluoroethyl, $(C_5-C_6)$-cycloalkyl, $(C_5-C_6)$-cycloalkyl-$(C_1-C_2)$-alkyl, $(C_5-C_6)$-aryl, $(C_5-C_6)$-aryl-$(C_1-C_2)$-alkyl, $H_2N$, $R^8R^8NR^9$, $R^8NHC(O)R^9$, $H_2N-C(=NH)$ or $H_2N-C(=NH)-NH-$;

where two adjacent substituents $R^{12}$ can also be $-OCH_2O-$ or $-OCH_2CH_2O-$;

$R^{16}$ is $(C_{10}-C_{14})$-cycloalkyl or $(C_{10}-C_{14})$-cycloalkyl-$(C_1-C_4)$-alkyl;

n is 1 or 2; and q is 0 or 1;

in all its stereoisomeric forms and mixtures thereof in all proportions, and its physiologically tolerated salts.

5. A compound of the formula I as claimed in claim 1, in which the distance between $R^{10}$ and the first N atom in A is from 12 to 13 covalent bonds along the shortest route between these atoms, in all its stereoisomeric forms and mixtures thereof in all proportions, and its physiologically tolerated salts.

6. A process for preparing a compound of the formula I as claimed in claim 1, which comprises linking, by means of fragment condensation, two or more fragments which can be derived retrosynthetically from the formula I.

7. A pharmaceutical preparation, comprising at least one compound of the formula I as claimed in claim 1, and/or its physiologically tolerated salts, in addition to pharmaceutically unobjectionable carrier and auxiliary substances.

8. A method for the treatment or prophylaxis of osteoporosis comprising administering to a subject in need thereof an effective amount of at least one compound as claimed in claim 1.

9. A method for the treatment or prophylaxis of cancer comprising administering to a subject in need thereof an effective amount of at least one compound as claimed in claim 1.

10. A method for inhibiting bone resorption by osteoclasts, inhibiting tumor growth or tumor metastasis, inhibiting inflammation, or for the treatment or prophylaxis of cardiovascular diseases, for the treatment or prophylaxis of neuropathies or retinopathies, or as a vitronectin receptor antagonist for the treatment or prophylaxis of diseases which are based on the interaction between vitronectin receptors and their ligands in cell-cell or cell-matrix interaction processes comprising administering to a subject in need thereof an effective amount of at least one compound as claimed in claim 1.

11. A pharmaceutical preparation, comprising at least one compound of the formula I as claimed in claim 1, and/or its physiologically tolerated salts, in addition to at least one pharmaceutically tolerable carrier, excipient, and/or additives.

12. The compound of the formula 1 as claimed in claim 1, wherein $R^{16}$ is 1-adamantyle or 2-adamantyle.

* * * * *